United States Patent
Van Urk et al.

(10) Patent No.: US 7,993,877 B2
(45) Date of Patent: Aug. 9, 2011

(54) PROCESS FOR THE PURIFICATION OF RECOMBINANT ALBUMIN

(75) Inventors: Hendrik Van Urk, Roden (NL); David John Mead, Radcliffe On Trent (GB); Philip Harvey Morton, West Bridgford (GB); Andrew John Cartwright, Muckamore (GB); Jason Cameron, Nottingham (GB); David James Ballance, Berwyn, PA (US); Michel Gaston Joseph Grandgeorge, Lyons (FR); Stephen Berezenko, Loughborough (GB); John Rodney Woodrow, West Bridgford (GB); Darrell Sleep, West Bridgford (GB); Jean-Luc Bernard Veron, Saint-Foy-les-Lyon (FR)

(73) Assignee: Novozymes Biopharma DK A/S (DK)

( * ) Notice: Subject to any disclaimer, the term of this patent is extended or adjusted under 35 U.S.C. 154(b) by 86 days.

(21) Appl. No.: 12/207,325

(22) Filed: Sep. 9, 2008

(65) Prior Publication Data

US 2009/0171070 A1    Jul. 2, 2009

Related U.S. Application Data

(63) Continuation of application No. 09/890,297, filed as application No. PCT/GB00/00257 on Jan. 31, 2000, now abandoned.

(30) Foreign Application Priority Data

Jan. 30, 1999   (GB) .................... 9902000.0

(51) Int. Cl.
  *C12N 15/14* (2006.01)
  *C07K 14/00* (2006.01)
(52) U.S. Cl. ....... 435/69.6; 530/362; 530/364; 530/412; 530/414; 514/4; 514/12; 514/21
(58) Field of Classification Search .................. None
See application file for complete search history.

(56) References Cited

U.S. PATENT DOCUMENTS

| | | |
|---|---|---|
| 2,433,905 A | 1/1948 | Hughes |
| 3,992,367 A | 11/1976 | Plan et al. |
| 4,007,113 A | 2/1977 | Ostreicher |
| 4,043,997 A | 8/1977 | Schroeder |
| 4,075,197 A | 2/1978 | Schuck et al. |
| 4,086,222 A | 4/1978 | Lindquist et al. |
| 4,222,934 A | 9/1980 | Hao |
| 4,228,154 A | 10/1980 | Fisher et al. |
| 4,289,690 A | 9/1981 | Pestka et al. |
| 4,350,156 A | 9/1982 | Malchesky et al. |
| 4,391,801 A | 7/1983 | Ng et al. |
| 4,675,384 A | 6/1987 | Dromard et al. |
| 4,748,120 A | 5/1988 | Wiesehahn |
| 4,990,447 A | 2/1991 | Konig et al. |
| 5,250,662 A | 10/1993 | Chang |
| 5,260,308 A | 11/1993 | Poduslo et al. |
| 5,277,818 A | 1/1994 | Matsuoka et al. |
| 5,284,777 A | 2/1994 | Rosenthal et al. |
| 5,330,901 A | 7/1994 | Prevatt et al. |
| 5,334,512 A | 8/1994 | Kobayashi et al. |
| 5,346,992 A | 9/1994 | Grandgeorge et al. |
| 5,372,997 A | 12/1994 | Inoue |
| 5,440,018 A | 8/1995 | Ohmura et al. |
| 5,561,115 A | 10/1996 | Tenold |
| 5,612,196 A | 3/1997 | Becquart et al. |
| 5,612,197 A | 3/1997 | Ohda et al. |
| 5,616,691 A | 4/1997 | Takahashi |
| 5,625,041 A | 4/1997 | Johnson et al. |
| 5,631,145 A | 5/1997 | Kobayashi et al. |
| 5,728,553 A | 3/1998 | Goodey et al. |
| 5,759,819 A | 6/1998 | Kobayashi et al. |
| 6,034,221 A | 3/2000 | Berezenko et al. |
| 6,638,740 B1 * | 10/2003 | Goodey et al. ............... 435/69.6 |
| 7,001,885 B2 | 2/2006 | Adachi et al. |
| 7,223,561 B2 * | 5/2007 | Goodey et al. ............... 435/69.1 |

FOREIGN PATENT DOCUMENTS

| | | |
|---|---|---|
| AT | 317 418 | 8/1974 |
| DE | 2 422 426 | 11/1974 |
| DE | 25 37 123 | 3/1977 |
| EP | 17 853 | 10/1980 |
| EP | 73 646 | 3/1983 |
| EP | 144 714 | 6/1985 |
| EP | 244 998 | 11/1987 |
| EP | 249 483 | 12/1987 |
| EP | 0 315 944 | 5/1989 |
| EP | 0 319 067 | 6/1989 |
| EP | 361 991 | 4/1990 |
| EP | 367 220 | 5/1990 |
| EP | 402 205 | 12/1990 |
| EP | 420 007 | 4/1991 |
| EP | 422 769 | 4/1991 |
| EP | 428 758 | 5/1991 |
| EP | 452 753 | 10/1991 |
| EP | 464 590 | 1/1992 |
| EP | 498 133 | 8/1992 |

(Continued)

OTHER PUBLICATIONS

Yasukawa, et al.; (1992) J Chromatography 597: 271-275.
Miksik and Deyl (1997) J Chromatography B 699: 311-345.
U.S. Appl. No. 09/890,297, Sep. 5, 2003, Non-Final Office Action.
U.S. Appl. No. 09/890,297, Feb. 9, 2004, Reply to Office Action.
U.S. Appl. No. 09/890,297, Apr. 13, 2004, Final Office Action.
U.S. Appl. No. 09/890,297, Sep. 13, 2004, RCE/Reply to Office Action.

(Continued)

*Primary Examiner* — Anand U Desai
(74) *Attorney, Agent, or Firm* — Ballard Spahr LLP

(57) ABSTRACT

A process is provided for the preparation of a highly pure recombinant albumin solution having a nickel ion content of less than 100 ng per gram of albumin. The process comprises subjecting a recombinant albumin to a series of chromatography, concentration, and diafiltration steps.

63 Claims, 17 Drawing Sheets

FOREIGN PATENT DOCUMENTS

| | | |
|---|---|---|
| EP | 524 681 | 1/1993 |
| EP | 559 895 | 9/1993 |
| EP | 570 916 | 11/1993 |
| EP | 612 761 | 8/1994 |
| EP | 656 419 | 6/1995 |
| EP | 685 491 | 12/1995 |
| EP | 699 687 | 3/1996 |
| GB | 2 053 926 | 2/1981 |
| GB | 2214508 | 9/1989 |
| JP | 63/083100 | 4/1988 |
| JP | 2 982 296 | 7/1992 |
| JP | 04/187 700 | 7/1992 |
| WO | 90/05533 | 5/1990 |
| WO | 90/15995 | 12/1990 |
| WO | 91/00290 | 1/1991 |
| WO | 92/04367 | 3/1992 |
| WO | 92/09303 | 6/1992 |
| WO | 93/17045 | 9/1993 |
| WO | 94/04687 | 3/1994 |
| WO | 94/26873 | 11/1994 |
| WO | WO 95/23857 | 9/1995 |
| WO | 9608501 A | 3/1996 |
| WO | 96/37515 | 11/1996 |
| WO | 97/31947 | 9/1997 |
| WO | WO 99/19740 | 4/1999 |
| WO | 02/051979 | 7/2002 |

OTHER PUBLICATIONS

U.S. Appl. No. 09/890,297, Mar. 10, 2005, Non-Final Office Action.
U.S. Appl. No. 09/890,297, Aug. 12, 2005, Reply to Office Action.
U.S. Appl. No. 09/890,297, Nov. 14, 2005, Non-Final Office Action.
U.S. Appl. No. 09/890,297, May 18, 2006, Reply to Office Action.
U.S. Appl. No. 09/890,297, Aug. 8, 2006, Final Office Action.
U.S. Appl. No. 09/890,297, Jan. 8, 2007, RCE/Reply to Office Action.
U.S. Appl. No. 09/890,297, Mar. 22, 2007, Non-Final Office Action.
U.S. Appl. No. 09/890,297, Jun. 12, 2007, Reply to Office Action.
U.S. Appl. No. 09/890,297, Aug. 20, 2007, Non-Final Office Action.
U.S. Appl. No. 09/890,297, Jan. 17, 2008, Reply to Office Action.
U.S. Appl. No. 09/890,297, Apr. 9, 2008, Final Office Action.
U.S. Appl. No. 07/949,601, May 4, 1993, Non-Final Office Action.
U.S. Appl. No. 07/949,601, Nov. 3, 1993, Response to Office Action.
U.S. Appl. No. 07/949,601, Nov. 9, 1993, Supplemental Response to Office Action.
U.S. Appl. No. 07/949,601, Feb. 1, 1994, Final Office Action.
U.S. Appl. No. 07/949,601, Jun. 1, 1994, Response to Final Office Action.
U.S. Appl. No. 07/949,601, Jun. 8, 1994, Advisory Action.
U.S. Appl. No. 08/265,972, Dec. 15, 1994, Non-final Office Action.
U.S. Appl. No. 08/378,859, Sep. 17, 1996, Non-final Office Action.
U.S. Appl. No. 08/378,859, Mar. 14, 1997, Response to Non-final Office Action.
U.S. Appl. No. 08/378,859, Jun. 25, 1997, Notice of Allowance.
U.S. Appl. No. 08/952,558, Dec. 19, 2000, Non-Final Office Action.
U.S. Appl. No. 08/952,558, Jun. 19, 2001, Reply to Non-Final Office Action.
U.S. Appl. No. 08/952,558, Nov. 2, 2001, Non-Final Office Action.
U.S. Appl. No. 08/952,558, Dec. 18, 2001, Reply to Non-Final Office Action.
U.S. Appl. No. 08/952,558, Apr. 8, 2002, Final Office Action.
U.S. Appl. No. 08/952,558, Jul. 2, 2002, Reply to Final Office Action.
U.S. Appl. No. 08/952,558, Aug. 13, 2002, Notice of Allowance.
U.S. Appl. No. 08/952,558, Feb. 14, 2003, Supplemental Submission for RCE.
U.S. Appl. No. 08/952,558, Apr. 11, 2003, Notice of Allowance.
U.S. Appl. No. 08/952,558, Jun. 23, 2003, Amendment After Allowance.
U.S. Appl. No. 09/970,648, May 12, 1998, Notice of Allowance.
U.S. Appl. No. 09/970,648, Mar. 11, 1999, Notice of Allowance.
U.S. Appl. No. 10/301,357, Dec. 22, 2003, Non-Final Office Action.
U.S. Appl. No. 10/873,504, Oct. 5, 2005, Non-Final Office Action.
U.S. Appl. No. 10/873,504, Apr. 7, 2006, Reply to Office Action.
U.S. Appl. No. 10/873,504, Jun. 13, 2006, Final Office Action.
U.S. Appl. No. 10/873,504, Dec. 18, 2006, Reply to Office Action.
U.S. Appl. No. 10/873,504, Jan. 17, 2007, Notice of Allowance.
U.S. Appl. No. 10/873,504, Feb. 26, 2007, Amendment After Allowance.
U.S. Appl. No. 10/873,504, Mar. 27, 2007, Response to Rule 312 Communication.
U.S. Appl. No. 11/738,582, Apr. 4, 2008, Non-Final Office Action.
U.S. Appl. No. 11/738,582, Aug. 1, 2008, Reply to Office Action.
U.S. Appl. No. 11/738,582, Nov. 4, 2008, Non-Final Office Action.
U.S. Appl. No. 11/738,582, Feb. 27, 2009, Reply to Office Action.
U.S. Appl. No. 11/738,582, Jun. 1, 2009, Notice of Allowance.
Reiss et al. (1980) Nickel Toxicol., Proc. Int. Conf., 2ND, pp. 91-94.
Sarkar (1980), Nato Adv. Study Inst. Ser. C, Bioenerg. Thermodyn. Model. Syst., 55:23-32.
Goward et al. (1990), Biochem. J. 267:171-177.
Travis et al (1976) Biochem J. 157, 301-306.
Okabayashi et al (1991) J. Biochem. 110, 103-110 (Green Cross).
Harrison (1988) Biochem J. 252, 865-874.
Linn (1990) Methods in Enzymology 182, 9-15.
Pohl (1990) Methods in Enzymology 182, 68-83.
Rossomando (1990) Methods in Enzymology 182, 309-328.
Stellwagen (1990) Methods in Enzymology 182, 343-357.
Stoltz et al (1991) Pharmaceut. Tech. Int. Jun. 1991, 60-65.
More & Harvey (1991) in "Blood Separation and Plasma Fractionation", Ed. Harris, Wiley-Liss, pp. 261-306.
Maurel et al (1989) in "Biotechnology of Plasma Proteins" Eds. Stoltz & Rivat, Colloque Inserm, 175, 19-24.
Finlayson "Physical and Biochemical Properties of Human Albumin" in Proceedings of the Workshop on Albumin, Bethesda, NIH, 1976, 31-56.
Fürst et al (1989) Beitr. Infusionsther. 24, 83-90 (supplied with English translation).
Allary et al (1991) Bioseparation 2, 167-175.
Meireles et al (1991) Biotech. & Bioeng. 38, 528-534.
Stoltz et al (1989) in "Biotechnology of Plasma Proteins" Eds Stoltz & Rivet, Colloque Inserm 175, 19-24.
Tayot et al (1987) Develop. Biol. Standard. 67, 15-24.
Berglöf et al (1983) J. App. Biochem. 5, 282-292.
Andersson et al (1987) J. Chromat. 421, 141-146.
Ng et al (1978) J. Pharm. Sci. 67, 431-433.
Hao (1979) Vox Sang. 36, 313-320.
Fell & Maharaj (1986) The Lancet Aug. 23, 1986, 467-468.
Köppel et al (1988) Clin. Toxicol. 26, 337-356.
Sleep et al (1990) Bio/Technology 8, 42-46.
Fleer et al (1991) Bio/Technology 9, 968-975.
Latta et al (1987) Bio/Technology 5, 1309-1314.
Sijmons et al (1990) Bio/Technology 8, 217-221.
Saunders et al (1987) J. Bact. 169, 2917-2925.
Etcheverry et al (1986) Bio/Technology 4, 726-730.
Sleep et al (1991) Bio/Technology 9, 183-187.
Grandgeorge & Pelloquin (1989) Transfusion 29, 629-634.
Polson et al (1983) Prep. Biochem. 13, 137-159.
Stoltz et al (1987) Bio-Sciences 6, 103-106.
Curling (1980) in "Methods of Plasma Protein Fractionation" Ed. Curling, Academic Press.
Gammelgaard & Sandberg (1989) J. Trace Element Electrolytes Health Dis. 3, 39 42.
Co-Sarno et al (1983) J Chromatog. 266, 105-113.
Subramanian (1984) CRC Critical Rev. Biochem. 16, 169-205.
Boeden et al (1991) J Chromatog. 552, 389-414.
Quirk et al (1989) Biotech. & App. Biochem. 11, 273-287.
van Liederkerke et al (1991) J. Pharm. Sci. 80, 11-16.
Wichman & Andersson (1974) Biochem. Biophys. Acta 372, 218-224.
Nesbakken (1982) "Comparative Study of Different Preparations of Human Albumin for Clinical Use", in "Compte-rendu de la réunion coopération internationale et dérivés sanguins", 1981, Annecy, France; Fondation Mérieux, Lyons.
Tayot et al (1982) "Comparative Study of Different Preparations of Human Albumin for Clinical Use", in "Compte-rendu de la réunion coopération internationale et dérivés sanguins", 1981, Annecy, France; Fondation Mérieux, Lyons.
Dodsworth et al (1996) Biotechnol. Appl. Biochem. 24, 171-176.
Peters et al (1973) J. Biol. Chem. 248, 2447-2451.

Aslam et al (1976) Anal. Biochem. 75(1), 329-335.
Sundberg & Porath (1974) J. Chromatog. 90, 87-98.
"Affinity Chromatography", Pharmacia booklet, 1979, pp. 9, 12 and 27.
Organikum, VEB Deutcher Verlag der Wissenschaften, 5 Auflage, 1965, p. 250.
98. Unger (1989) HanDBOuch der HPLC, GIT Verlag, pp. 74-75.
Atkinson & Mavituna (1991) Biochem. Eng. Biotechnol. HanDBOook (2nd Ed) Stockton Press: 935-937.
Bertholf et al (1984) Biochem. & Biophys. Res. Comm. 125(3), 1020-1024.
Cohn et al (1946) J. Am. Chem. Soc. 68, 459.
Dawson et al (1993) Data for Biochem. Res. (3rd Ed), Oxford University Press, Oxford, UK: 503-504.
Lee et al (1989) Applied Biochem. & Biotechnol. 22(1), 1-11.
Milliner et al (1985) New Eng. J. Med. 312(21), 1389-1390.
Milliner et al (1985) New Eng. J. Med. 312(3),165-167.
Olson & Kent (1989) Transfusion 29(1), 86-87.
Perry et al (1984) Perry's Chemical Engineering Handbook (6th Ed), McGraw-Hill Inc., New York, USA: 19.72-19.73.
Petrie et al (1984) Am. J. Kid. Dis. IV, 1, 69-74.
Quagliaro et al (1988) J. Parenteral Sci. & Tech. 42(6),187-190.
Sattar et al (1979) Water Res. 13(7), 637-643.
Victor et al (1988) Transfusion 28(3), 290-291.
Kawabe (1991) "Study Reports of Anti-AIDS Drug Development", Japan Health Sciences Foundation, Tokyo.
Shaklai et al (1984) J Biol. Chem. 259, 3812-3817.
Beneš et al (1993) "Affinity Chromatography with Immobilized Benzeneboronates", in Molecular Interactions in Bioseparations, Ed. That T Ngo, Plenum Press, New York.
Voet et al, Biochemistry, John Wiley & Sons, Inc 1990:570-71.
Alberts et al, Molecular Biology of the Cell, 1989:456.
Ion Exchange Chromatography. Principles and methods. 3rd edition (1991), Pharmacia ISSN: 9197049034 ISBN: 9-197-04903-4.
Protein Purification: Principles and Practice. 3rd edition. Springer-Verlag, New York ISBN: 0-387-94072-3, (1993).
Strahl-Bolsinger et al (1993) PNAS USA 90, 8164-8168.
Immervoll et al (1995) Yeast 11, 1345-1351.
Bourdineaud et al (1998) Molecular Microbiology 27(1), 85-98.
Gentzsch et al (1995) FEBS Letters 377, 128-130.
Strahl-Bolsinger et al (1991) Eur J Biochem 196, 185-190.
Gentzsch et al (1997) Glycobiology 7(4), 481-486.
Gentzsch et al (1996) The EMBO Journal 15(21), 5753-5759.
Nakayama et al (1998) Biochimica and Biophysica Acta 1425, 255-262.
Strahl-Bolsinger et al (1992) 16th International Conference on Yeast Genetics and Molecular Biology.
Shukun et al (1988) Journal of Chromatography 432, 137-151.
Pande et al (1992) Analytical Biochemistry 204, 103-106.
Stellwagen (1990) Methods in Enzymology 182, 317-29.
King (1987) Transfusion 27, 302-308.
Hansen & Ezban (1981) Develop. Biol. Stand. 48, 1005-1112.
He & Carter (1992) Nature 358, 209-215.
Geisow et al (1991) Techniques in Protein Chemistry, II Ed. Villafranca, Academic Press, 567-573.
Geisow et al (1983) Tibtech 8, 301-303.
Rhodes et al (1990) Meth. Enzymol. 182, 555-565.
Ringe et al (1996) "A Consumer's Guide to Protein Crystallography", Protein Engineering and Design Paul R. Carey (ed), 205-229.
Kawabe (1990) "Study on the Development of a Human Serum Albumin Production System with Recombinant DNA Technology" Japan Health Sciences Foundation, Tokyo, Japan, Study Reports on Anti-AIDS Drug Development.
Vidal (1989) High-Performance Liquid Chromatofocusing and Column Affinity Chromatography of In Vitro 14C-Glycated Human Serum Albumin, Elsevier Science Publishers B.V., 467-475.
Ohtani, Wataru, et al.; Analysis of Pichia pastoris Components in Recombinant Human Serum Albumin by Immunological Assays and by HPLC with Pulsed Amerometric Detection; Anal. Chem. 1998, 70, 425-429.
Strahl-Bolsinger, Sabine, et al.; Protein O'mannosylation; Biochimica et Biophysica Acta 1426 (1999) 297-307.
Miksik et al.: Post-translatin non-enzymatic modification of proteins II. Seperation of selected protein species after glycation and other carbonyl-mediated modifications; J. Chromatogr. B, 699 (1997).
Yasukawa et al.: High-performance affinity chromatography system for the rapid, efficient assay of glycated albumin; Journal of Chromatography, 597 (1992).

* cited by examiner

5'-GATTGGCAGAAGAGGTATCTGCTTATGGACATGAGGGGCTTTGGCGGT
GATGCCAATGATGACTTTGTTGTGGAGATTGCCAAGGATCTTTCAACTAC
TGAAGAAGCTAAGGAAAACGTTAGGGCCATTCAAACTGTTTTTAGATTGA
GACATGCGATGACTGGTTGTTACTTGTTCTCCCACGAAGTCAAGCTTCCC
AAGTGGGCATATGAGCAACAAGAGGTTACTTGTGCTACTCAAGGTATCAA
ACCCTATCTTACTGGTACGTTGAGACCAACGAAACCCATTCTTGGATAA
AGAGGTTGATGAAATAGTTAGCTATCCTGTTCCGACTTTCTTTCAAAGGTT
GCCGACTCACGCCAGAATGTGGAAGATCAACAAGGCTTACTGATCATATG
CTATGAATCCAGTCCAGATCTTGG-3'

Fig. 10

SEQ ID NO:1

5'-GTGTTGCAGTTGTAGTCCCACTTGAGTATCTTGGATTCGTTGCATTGGT
CCTTGGTCCATCGTCCTGCATAGATCAATGGGAGAATATCTTTGGAAGAT
AGAAAGCGCAACGGCAAAAAGAGAACGAATATGGAGTAAGACACAACC
TGTTTGTTTTTGAAGACATAAGAGTGAATAATCTCAAACACATGTCCGAG
AGCCAATATACCAAAGTACAATGATGGTAGATAGTGGTGCAAAAATAGCT
GACGGGCCATAAGGGAAAGATGGCAAGTAATGCAGTACCCATCCTAGGA
TGTAATGAAGCATTTGAACATTGAAGTTGAGCACAGTTGGGTCAACGCTG
AACCCAAAACCTCTTTGCCTCTCAGAATAGAGAAACCAAAAAGACAGAG
AACAAAGCATACTTGCGGTGACTGTCACCAAGTGACAGCATTCCTATGAA
ATAAATTG-3'

Fig. 11

SEQ ID NO:2

5'-TACGTTATGGATGTGCATCCACTTCCTGAAGCTTCTCATCGGCAACCTT
TTGAATCTGCAATTTATTATCTTCATTGAAGGCAAGCTTGAACACTTTGAC
GGTAGAAAGACGAGCGACAACCAAGAATTGCCCGTCAGAAGTGAGATCA
CAATGGGTGATGTTGTCCTCATCGCTTAGGACCAGTTTGGCTAATAGTTTT
CTGCCTTGCTGAGGAAGGACTTTCCATACTTTAATGGTTTGGTCTTGCCCA
TGATCACCAGCTTCTGGGATTTATTGAAAGGACAGTTTGATCGTTTCAG
GGAATACTGACAGTCTTTGAATTTCGCAGTCTTGAAACGATTCAGCTTAG
AAACGGCTATGTCTGACAATGATGCTTCAGATAGTACAGATCGAGGTCCT
GGATTGG-3'

Fig. 12

SEQ ID NO:3

5'-GCGCAGGTGACTTCTTGCTGGAAAATGTGCTACAAGGAGGTAAAGACC
GTGTCATTGAGGGCCTGGTTTGGTCTACTTATGACGATTACCCTCGTCGTC
TGTTTTCCATTGGTGGTTCGACTGTGATGACCGAATGGGATATTGCTACCG
GTTTGCCCTTAAACAACTACGATTGTAACTCCGGTATCACCTGGAGTATC
AGCATCAACACAACTCAGGATAAGATATGCGTAGGCTGTGACAATGGAA
CTGTAGTCGTTATTGACATAAGTGGTGGACCGGGATCTCTAGTATAAGAA
AATTGTATCCGGATGTTCTGATGGCCGATAAGGATATGGAATACGAGGAA
G-3'

Fig. 13

SEQ ID NO:4

5'-GTATTGCAGTTGTAGTCCCAGAATGAATTGCTCTTTTAATTGTTCTTTTT
GGCTGGAGAAGTGCTCGTATGTCTTGATCGATGAGATACAGCTGAGATTT
AAGTTGTTCTAGGTTGATAGTTGAATGTTCAGAGTTGAGGGGTTCCATGG
TCAAGTATAGGAGGATCCAGCTCATCTAGGGAGTGGAATTGAGTACTGAC
ACTCATTACTGGAAGAAGTAGAAAGAGTACTGGTTTTGTGGTAAGTTCCA
TATTTCAGATGTCTGTAGATGGTCGAGCGAGGTGAACATTTCATAGGAGA
TTTCAGAGGAGTTGGACTTTGAAAATGGTGACAAAGGTAGACAGAAGA
AAGGTTAGAGAGTGCAGTGATTCAAGGTGGTTGCAGAAGTCC-3'

Fig. 14

SEQ ID NO:5

5'-TTGAGACATGCTATGACGGGTCAAGTTTTAGATAAAGTTGGACTCTTG
GGCATGAGCGCATCCTCACATCGGCCATAGCAGATAAACGGTAGCAGTTT
TTTTGAACGAGGCTGTAAGATAGGGGAATCTCCGTTTTAGGCTTTCAGTG
ACTTGTTGCATCGCAATGGGTAGATATGTTCACCAGTGGCAAAAGCTCTG
GATGCTATGAAACTGACCAAATGTGGATTAGAACTTGGAGTCTAACTATT
TGACTCTAAGAATTTCCAATTTTTGCCTTCTACTAGCCATTTTCTACTTTC
ATGGGACATCATCACTTATTTGCTCCCCAACCTGTCAAATACCCACCAAT
GTTCAAGGTCG-3'

Fig. 15

SEQ ID NO:6

5'-AGATTGAGACATGCTATGACGGGTTGTTACTTGTTCTCCCGCGAAGTCA
AGCTTCCCAAGTGGGCATATGAGCAACAAGAGGTTACTTGTGCTACTCAA
GGGTATCAAACCACTATCTTACTGGTACGTTGAGACCAACGAAAACCCAT
TCTTGGATAAAGAGGTTGATGAAATAGTTAGCTATCCTGTTCCGACTTTCT
TTCAAAAGGTTGCCGAGCTACACGCCAGAATGTGGAAGATCAACAAGGG
CTTAACTGATCATCATGTCTATGAATCCAGTCCAGATTCTTGGCCCTTCCT
GTCAGAGGTATAAGCTACTGGTCAAAAAATCACTCCAAATTATTTCATAG
GTAATGCTGCACTTGGTGGACAGTCACCGAAGTTTG-3'

Fig. 16

SEQ ID NO:7

5'-GTGTTGCAGTTGTAGTCCCACTTGAGTATCTTGGATTCGTTGCATTGGT
CCTTGGTCCATCGTCCTGCATAGATCAATGGGAGAATATCTTTGGAAGAA
GAAAGCGCAACGGCAAAAAGANAACGAATATGGAGTAAGACACAACCT
GTTTGTTTTGAAGACATAAGAGTGAATAATCTCAAACACATGTCCGAGA
GCCAATATACCAAAGTACAATGATGGTAGATAGTGGGTGCAAAAATAGCT
GACGGGCCATAAGGAAAGATGGCAAGTAATGCAGTACCCATCCTAGGAT
GTAATGAAGCATTTGAACATTGAAGTTGAACACAGTTGGGTCAACGCTGA
ACCCAAAACCTCTTTGCCATCTCAGAATAGAGAAAACCAAAAGACAGA
GAACAAAGCA-3'

Fig. 17

SEQ ID NO:8

PROCESS FOR THE PURIFICATION OF RECOMBINANT ALBUMIN

CROSS REFERENCE TO RELATED APPLICATIONS

This application is a continuation of application Ser. No. 09/890,297, Jan. 4, 2002, which is a national phase application filed from international patent application no. PCT/GB00/00257, filed Jan. 31, 2000, which claims the benefit of Great Britain patent application no. 9902000.0, filed Jan. 30, 1999, which applications are hereby incorporated herein by reference in their entirety.

The present invention relates to a process for purifying the protein human serum albumin (HSA) extracted from serum or plasma, or recombinant human albumin (rHA) produced by transforming or transfecting an organism with a nucleotide coding sequence encoding the amino acid sequence of human serum albumin, including rHA produced using transgenic animals or plants. In this specification, the term "albumin" refers generically to HSA and/or rHA.

INCORPORATION OF SEQUENCE LISTING

A computer readable form of the sequence listing, "16238-0004U2_Seq_List.txt" (20,480 bytes), submitted via EFS-WEB and created on Feb. 24, 2009, is herein incorporated by reference.

BACKGROUND OF THE INVENTION

Albumin is used to treat patients with severe burns, shock or blood loss. It is also used to supplement media used for growing higher eukaryotic cells and as an excipient for pharmacologically active compounds, many of which need to be stabilised. At present, the demand for the product is satisfied by albumin extracted from human blood. Examples of extraction and separation techniques include those disclosed in: JP 03/258 728 on the use of a cation exchanger; EP 428 758 oil the use of anion exchange; and EP 452 753 on the use of heating, adding salt and diafiltering.

The production of rHA in micro-organisms has been disclosed in EP 330 451 so and EP 361 991. Purification techniques for rHA have been disclosed in: WO 92/04367, removal of matrix-derived dye; EP 464 590, removal of yeast-derived colorants; EP 319 067, alkaline precipitation and subsequent application of the rHA to a lipophilic phase; and WO 96/37515, which contains several complete purification processes.

The present invention represents the result of intensive development of the processes described in WO 96/37515 and that of U.S. Pat. No. 5,728,553, incorporated herein by reference.

SUMMARY OF THE INVENTION

A first aspect of the present invention provides a process for purifying an albumin solution, the process comprising the step of subjecting a first albumin solution of pH8.0-9.5, and having a conductivity in the range of 1 to 75 mS·cm$^{-1}$, to an affinity chromatography step which is run in negative mode with respect to the albumin and which utilises an affinity matrix comprising immobilised dihydroxyboryl groups, thereby obtaining a purified albumin solution.

Preferably, the pH of the first albumin solution is pH8.0-9.0, and more preferably pH8.3-pH8.6. It is preferred that the first albumin solution is buffered with a buffer having a pH within the aforementioned pH ranges.

Preferably, the buffer comprises an amino acid at a concentration of 10-500 mM, preferably 25-200 mM, and more preferably 50-150 mM. Preferably the amino acid is glycine.

Preferably, the buffer comprises a monovalent cation at a concentration of 0-500 mM, preferably 25-200 mM, and more preferably 50-150 mM. Preferably, the monovalent cation is sodium, preferably in the form of NaCl. Accordingly, in a preferred embodiment the buffer comprises NaCl at a concentration of 0-500 mM, preferably 25-200 mM, and more preferably 50-150 mM.

Preferably, the buffer comprises a divalent cation at a concentration of 5-250 mM, preferably 10-100 mM. Preferably, the divalent cation is calcium, preferably in the form of $CaCl_2$. Accordingly, in a preferred embodiment the buffer comprises $CaCl_2$ at a concentration of 5-250 mM, preferably 10-100 mM.

In a particularly preferred embodiment the first albumin solution and/or buffer comprises about 100 mM glycine, about 100 mM NaCl and about 50 mM $CaCl_2$.

Preferably, the conductivity of the first albumin solution and/or buffer is 10-50 mS·cm$^{-1}$ and more preferably 18-22 mS·cm$^{-1}$.

Advantageously, the concentration of the albumin in the first albumin solution is in the range of 20-120 g·L$^{-1}$, preferably 70-120 g·L$^{-1}$, and more preferably 100±10 g·L$^{-1}$. Preferably, the albumin is loaded in less than 0.5 column volumes, more preferably in less than 0.35 column volumes.

Suitably, the matrix comprises a boronic acid. The term "acid" as used herein includes the salts thereof. Advantageously, the boronic acid is bonded via a triazine or a substituted triazine, for example to form monoborotriazine or diborotriazine, to a support such as agarose. Preferably, the boronic acid is aminophenylboronic acid.

Publications that cover alternatives to phenylboronate, such as aliphatic and substituted aromatic ligands, include Adamek, V. et al (1992) *J. Chrom.* 625, 91-99, Singhal, R E P et al (1991) *J. Chrom* 543, 17-38 and Liu, X. et al (1994) 687, 61-69.

Suitably, following the affinity chromatography step the purified albumin solution is subjected to further purification, preferably further chromatographic purification. Preferably, the albumin is further purified using cation exchange chromatography and/or anion exchange chromatography. The order of the cation and anion exchange steps can be interchanged while still performing their purification objectives. From an operational point of view, a better integrated process is cation exchange chromatography followed by anion exchange chromatography.

Suitably, the purified albumin solution produced according to the process of the first aspect of the present invention undergoes one or more of, buffer exchange; concentration; dilution; dialysis; diafiltration, pH-adjustment (preferably to a pH greater than pH2.0 or pH4.0, and preferably to a pH less than pH10.0); treatment with a reducing agent (eg as described in EP 570 916); decolouration treatment (eg with charcoal); heating (including sterilisation); cooling or conditioning; formulation for parenteral administration to a human; or placing into a final container.

By parenteral administration we include intravenous administration, subcutaneous administration and intramuscular administration. The albumin may function as an excipient for a pharmacologically active protein, which may be administered parenterally.

A "final container" is one which leaves the manufacturer and is distributed to customers such as hospitals and pharmacies.

A second aspect of the invention provides a process for purifying an albumin solution, the process comprising cation exchange chromatography and anion exchange chromatography, wherein the thus purified albumin solution optionally undergoes one or more of buffer exchange; concentration; dilution; dialysis; diafiltration; pH4-adjustment (preferably to a pH greater than pH2.0 or pH4.0, and preferably to a pH less than pH10.0); addition of reducing agent; decolouration treatment (eg with charcoal); heating (including sterilisation); cooling; or conditioning, but not further purification, in particular not further chromatographic purification, prior to being put into a final container.

The cation exchange chromatography step may follow the anion exchange chromatography step, or vice versa. Preferably, the cation exchange chromatography step is followed by the anion exchange chromatography step.

Preferably, between the anion and cation exchange steps, there is no further purification step, although the albumin may be subjected to buffer exchange etc. as noted above.

By conditioning, we mean any non-purifying handling step which improves the environment or condition of the albumin for the next step of the process or for final use. Conditioning can include the addition of an albumin stabiliser such as octanoate and/or other fatty acid, such as a $C_6$ or $C_{10}$ fatty acid, or sodium acetyl tryptophanate or mandelate. Conditioning can also include the addition of salts etc., and may involve adjusting the conductivity of the albumin solution.

The cation exchange step of the first and second aspects of the present invention may be run in negative or positive mode with respect to the albumin. In a preferred embodiment the cation exchange step is run in negative mode with respect to the albumin. Advantageously, the conditions are so chosen that glycosylated albumin binds more strongly to the cation exchange material than non-glycosylated albumin.

The cation exchange chromatography step of the first and second aspects of the present invention may utilise a commercial cation exchange matrix such as SP-Sepharose FF, SP-Spherosil, CM-Sepharose FF, CM-Cellulose, SE-Cellulose or S-Spheradex. Preferably, the cation exchange step utilises a matrix which comprises immobilised sulfopropyl substituents as cation exchangers.

Preferably, the albumin solution which undergoes cation exchange chromatography has a pH of 4.5-6.0, more preferably a pH of 5.0-5.6, and yet more preferably a pH of 5.2-5.4.

Preferably, the albumin solution which undergoes cation exchange chromatography has an albumin concentration of 10-250 g·L$^{-1}$, preferably 20-70 g·L$^{-1}$, and more preferably 50±10 g·L$^{-1}$.

Preferably, the albumin. solution which undergoes cation exchange chromatography has an octanoate ion concentration of 2-15 mM, preferably 5-10 mM, and more preferably 6-9 mM.

Conveniently, prior to the cation exchange step, the albumin solution undergoes one or more of the following processes: (i) pH-adjustment (preferably to a pH greater than pH2.0 or pH4.0, and preferably to a pH less than pH10.0); (ii) concentration; (iii) diafiltration; or (iv) conditioning by addition of a stabiliser such as octanoate and/or other fatty acid, such as a C6 or C10 fatty acid, or sodium acetyl tryptophanate or mandelate. Alternatively, or additionally, the albumin solution undergoes one or more of buffer exchange; dilution; dialysis; diafiltration; treatment with a reducing agent; decolouration treatment (eg with charcoal); heating; cooling; or conditioning.

Generally, any modification involves additions, not removals. Preferably, the pH of the albumin solution is adjusted by the addition of acetic acid. Preferably, the albumin solution is concentrated by ultrafiltration.

The anion exchange chromatography step of the first and second aspects of the present invention may utilise a commercial anion exchange matrix such as Q Sepharose-FF, QMA-Spherosil, DEAE-Spherodex, Q-Hyper D, DEAL-cellulose, QAE-cellulose, or TMAE, DMAE, or DEAE Fractogel. Preferably, the anion exchange step utilises a matrix which comprises immobilised dialkylaminoalkyl (for example diethylaminoethyl) substituents as anion exchangers.

In one preferred embodiment the anion exchange chromatography step of the no first and second aspects of the present invention is run in negative mode with respect to the albumin.

Preferably, the albumin solution which undergoes negative mode anion exchange chromatography has a pH of 4.0-5.2, more preferably a pH of 4.2-4.9, and yet more preferably a pH of 4.5-4.7.

Preferably, the albumin solution which undergoes anion exchange chromatography has a conductivity of less than 4.0 mS·cm$^{-1}$, and more preferably a conductivity of 1.0±0.5 mS·cm$^{-1}$ and yet more preferably 1.05±0.1 mS·cm$^{-1}$ Conveniently, prior to the anion exchange step, the albumin solution undergoes pH adjustment and/or dilution with water. Preferably, the pH of the albumin solution is adjusted with acetic acid.

In another preferred embodiment the anion exchange chromatography step of the first and second aspects of the present invention is run in positive mode with respect to the albumin.

Suitably the albumin solution which undergoes positive mode anion exchange chromatography has a pH of 6.0-8.0, preferably a pH of 6.5-7.5, and yet more preferably a pH of 6.8 to 7.2. Preferably, the albumin solution has been pH-adjusted using orthophosphate ions.

In one preferred embodiment the albumin concentration is 10-100 g·L$^{-1}$, more preferably 25-80 g·L$^{-1}$, and most preferably 30-60 g·L$^{-1}$. Preferably, the conductivity of the albumin solution is 1.0-2.0 mS·cm$^{-1}$, preferably 1.2-1.6 mS·cm$^{-1}$.

Suitably, the albumin is eluted from the anion exchanger with a buffer IC comprising 20-90 mM, preferably 30-70 mM and more preferably 35-65 mM of a phosphoric acid salt, for example sodium phosphate. Preferably, the albumin is eluted from the anion exchanger with a buffer of pH6.0-8.0, preferably pH6.5-7.5.

It is particularly preferred that the processes of the first and second aspects of the present invention are preceded by one or more of the following steps: fermentation; primary separation; centrate conditioning; cation exchange chromatography, preferably using sulfopropyl substituents as cation exchangers; anion exchange chromatography, preferably using diethylaminoalkyl substituents as anion exchangers; or affinity chromatography, preferably using an affinity matrix which comprises an immobilised albumin-specific dye, preferably a Cibacron Blue type of dye.

In a preferred embodiment of the present invention a process for purifying albumin is provided which comprises the following steps:

(a) subjecting an albumin solution to a cation exchange chromatography step run in positive mode with respect to the albumin;
(b) collecting an albumin-containing cation exchange eluate;
(c) subjecting the cation exchange eluate to an anion exchange chromatography step run in positive mode with respect to the albumin;
(d) collecting an albumin-containing anion exchange eluate;

(e) subjecting the anion exchange eluate to an affinity chromatography step run in positive mode with respect to the albumin;
(f) collecting an albumin-containing affinity chromatography eluate;
(g) subjecting the affinity chromatography eluate to an affinity chromatography step run in negative mode with respect to the albumin and in positive mode with respect to glycoconjugates (glycosylated albumin and/or glycoproteins);
(h) collecting the albumin-containing affinity chromatography flow through;
(i) subjecting the affinity chromatography flow through to a cation exchange chromatography step run in negative mode with respect to the albumin;
(j) collecting the albumin-containing cation exchange flow through;
(k) subjecting the cation exchange flow through to an anion exchange chromatography step run in negative mode or positive mode;
(l) collecting the albumin-containing anion exchange flow through wherein the anion exchange step is ran in negative mode; or eluting from the anion exchange matrix an anion exchange eluate wherein the anion exchange step is run in positive mode;
and wherein any of the respective purification steps are optionally preceded or followed by one or more of: buffer exchange; concentration; dilution; dialysis; diafiltration; pH-adjustment (preferably to a pH greater than pH2.0 or pH4.0, and preferably to a pH less than pH10.0); treatment with a reducing agent; decolouration treatment (eg with charcoal); heating (including sterilisation); cooling; or conditioning.

Accordingly, the purification steps may or may not be separated by one or more of: buffer exchange; concentration; dilution; dialysis; diafiltration; pH-adjustment; treatment with a reducing agent; decolouration treatment; heating; cooling; or conditioning.

When any step is run in the negative mode for albumin, washings may be collected as well as flow through.

In another preferred embodiment of the present invention a process for purifying albumin is provided which comprises the following steps.
(a) subjecting an albumin solution to a cation exchange chromatography step run in positive mode with respect to the albumin;
(b) collecting an albumin-containing cation exchange eluate;
(c) subjecting the cation exchange eluate to an anion exchange chromatography step run in positive mode with respect to the albumin;
(d) collecting an albumin-containing anion exchange eluate;
(e) subjecting the anion exchange eluate to an affinity chromatography step run in positive mode with respect to the albumin;
(f) collecting an albumin-containing affinity chromatography eluate;
(g) subjecting the affinity chromatography eluate to an affinity chromatography step run in negative mode with respect to the albumin and in positive mode with respect to glycoconjugates;
(h) collecting the albumin-containing affinity chromatography flow through;
(i) subjecting the affinity matrix flow through to an anion exchange chromatography step run in negative or positive mode with respect to the albumin;
(j) collecting the albumin-containing anion exchange flow through wherein the anion exchange step is run in negative mode; or eluting from the anion exchange matrix an anion exchange eluate wherein the anion exchange step is run in positive mode;
(k) subjecting the albumin solution purified by the anion exchange chromatography step to a cation exchange chromatography step run in negative mode with respect to the albumin;
(l) collecting the albumin-containing cation exchange flow through;
and wherein any of the respective purification steps are optionally preceded or followed by one or more of: buffer exchange; concentration; dilution; dialysis; diafiltration; pH-adjustment (preferably to a pH greater than pH2.0 or pH4.0, and preferably to a pH less than pH10.0); treatment with a reducing agent; decolouration treatment (eg with charcoal); heating (including sterilisation); cooling; or conditioning.

Accordingly, the purification steps may or may not be separated by one or more of: buffer exchange; concentration; dilution; dialysis; diafiltration; pH-adjustment; treatment with a reducing agent; decolouration treatment; heating; cooling; or conditioning.

Preferably, prior to the positive mode cation exchange step of the invention, the albumin solution is conditioned as above. Preferably, the octanoate is added thereto to a final concentration of from about 1-10 in M and the pH is adjusted to about 4.0-5.0.

Advantageously, the albumin retained in the positive cation exchange step is washed with a high salt solution (eg 0.5-3.0M NaCl buffered at pH3.5 to 4.5, preferably at about pH 4.0, with 10-100 mM, preferably 20-40 mM, for example 25-30 mM sodium acetate) before being eluted.

Preferably, the albumin is eluted in the cation exchange step using a buffer containing a compound having a specific affinity for albumin, especially an acid, for example octanoate or another fatty acid, for example $C_6$ or $C_{10}$.

Suitably, the albumin is eluted from the anion exchanger, of the first anion exchange step, with a buffer containing a high level (e.g. at least 50 mM, preferably 50-200 mM, for example 80-150 mM) of a boric acid salt, for example sodium or potassium tetraborate.

Preferably, the positive mode affinity chromatography step uses a resin comprising an immobilised albumin-specific dye, such as a Cibacron Blue type of dye, preferably immobilised on the resin via a spacer such as 1,4-diaminobutane or another spacer of $C_{1-8}$, preferably $C_{1-6}$, eg $C_{1-5}$ and Lost preferably $C_4$ length, preferably having $\alpha,\omega$-diamino substitution. Preferably, the matrix is the "Delta Blue Matrix" (DBA), prepared as described in WO 96/37515.

A third aspect of the present invention provides a process for reducing the level of nickel ions in an albumin solution, the process comprising subjecting the albumin solution to a pH of 2.5 to 7.5, preferably 2.5-6.0, and removing nickel ions. Preferably, the albumin solution is subjected to a pH of 4.0 to 7.5, preferably 4.0 to 6.0, more preferably pH4.0 to 5.5, yet more preferably pH4.0 to pH5.0, and most preferably to pH4.0 to 4.5.

Preferably, the process of the third aspect of the invention comprises diafiltration against a buffer of pH2.5-6.0, or against a buffer having a pH within one of the aforementioned pH ranges. Alternatively, nickel removal can be achieved using gel permeation chromatography with a buffer having a pH within one of the above-listed pH ranges. Gel permeation chromatography may be performed using Sephaeryl S200 HR. Preferably, the buffer comprises acetate and/or malate ions. Alternatively, there is sufficient buffering capacity from albumin to adjust the pH and perform diafiltration/gel permeation chromatography with water.

The nickel ions can alternatively be chelated and removed from the albumin. This can be achieved using a chelating agent such as iminodiacetic acid immobilised on Sepharose (Chelating Sepharose, Pharmacia) or another polymer (such as Chelex, Bio Rad Laboratories) at a low pH, preferably pH 4.0 to 6.0, more preferably pH4.0 to 4.5.

Preferably, when the product from the process of the third aspect of the invention is subjected immediately to negative cation exchange chromatography it is preferred that the third aspect of the invention comprises subjecting the albumin solution to a pH of 5.0-5.6. Conversely, when the product from the process of the third aspect of the invention is not subjected immediately to negative anion exchange chromatography it is preferred that the third aspect of the invention comprises subjecting the albumin solution to a pH of 4.3-4.9.

In a preferred embodiment of the first, second and third aspects of the present invention the initial albumin solution is derived from a fungal culture medium obtained by culturing a fungus transformed with an albumin-encoding nucleotide sequence in a fermentation medium, whereby said fungus expresses albumin and secretes it into the medium. The fungus may be a filamentous fungus such as an *Aspergillus* species. Preferably, the fungus is a yeast. More preferably the fungus is of the genus *Saccharomyces* (eg *Saccharomyces cerevisiae*), the genus *Kluyveromyces* (eg *Kluyveromyces lactis*) or the genus *Pichia* (eg *Pichia pastoris*).

Preferably, at least some of the albumin purified in accordance with the first, second or third aspects of the present invention is produced by a cell according to the fifth aspect of the invention or a process according to the sixth aspect of the invention.

A fourth aspect of the present invention provides an albumin solution obtainable by a process according to any one of the preceding aspects of the present invention. Preferably, the albumin solution comprises recombinant albumin which exhibits one or more of the following properties:
(1) less than 0.5% (w/w) binds to Concanavalin A, preferably less than 0.2% or 0.15%;
(2) a glycation level of less than 0.6 moles hexose/mole of protein, and preferably less than 0.10, 0.075 or 0.05 moles hexose/mole of protein.

A purified albumin solution prepared by a process of the present invention may be further processed according to its intended utility. For example, it may be ultrafiltered through an ultrafiltration membrane to obtain an ultrafiltration retentate having an albumin concentration of at least about 10 g, preferably at least 40 g or more preferably about 80 g, albumin per liter, with the ultrafiltration retentate being diafiltered against at least 5 retentate equivalents of water.

A fifth aspect of the present invention provides a DNA sequence, plasmid or cell which comprises a recombinant albumin coding sequence wherein the 3' end of the recombinant albumin coding sequence comprises two or more in-frame translation stop codons, and preferably three in-frame translation stop codons.

The recombinant cells of the fifth aspect of the present invention may be eukaryotic or prokaryotic. The recombinant cells may be bacteria (for example *E. coli* or *Bacillus subtilis*), yeasts (for example a yeast of the genus *Saccharomyces* (eg *S. cerevisiae*), the genus *Kluyveromyces* (eg *K. lactis*) or the genus *Pichia* (eg *P. pastoris*)), filamentous fungi (for example *Aspergillus*), plants or plant cells, animals or animal cells (which may be transgenic) or insect cells.

A sixth aspect of the present invention provides a process for producing recombinant albumin, the process comprising culturing a fungal cell expressing a recombinant albumin coding sequence and obtaining the albumin, wherein the cell has a genetic modification which causes the cell to have at least a reduced capacity of mannosylation of the recombinantly-expressed albumin and wherein the culture medium is at least 1,000 L and is of pH6.0-6.8.

In the meaning of the present invention, genetic modification preferably means any suppression, substitution, deletion or addition of one or more bases or of a fragment of the fungal cell DNA sequences. Such genetic modifications may be obtained in vitro (directly on isolated DNA) or in situ, for example by genetic engineering techniques or by exposing the fungal cells to mutagenic agents. Mutagenic agents include for example physical agents such as energetic rays X-rays, γ-rays, UV, etc.) or chemical agents capable of reacting with different functional groups of DNA, such as alkylating agents (EMS, NQO, etc.) bisalkylating agents, intercalating agents, etc. Genetic modifications may also be obtained by genetic disruption, for example according to the method disclosed by Rothstein et al. [*Meth. Enzymol.* 194 (1991), 281-301]. According to this method, part or all of a gene is replaced, through homologous recombination, by an in vitro modified version. Genetic modifications can also be obtained by any mutational insertion on DNA sequences, such as transposons, phages, etc.

It is known that certain modifications such as point mutations can be reversed or attenuated by cellular mechanisms. Such modifications may not provide the most useful forms of modified fungal cells of this invention since their phenotypical properties may not be very stable. Accordingly, it is preferred that the genetic modification(s) are stably inherited and/or are non-reverting and/or are non-leaky. Such modification(s) are generally obtained by a deletion or a gene disruption.

By a "leaky mutant" and grammatical variants thereof, we include mutants that result from a partial rather than a complete inactivation of the wild-type function.

The genetic modification(s) carried by the fungal cells of the invention may be located in a coding region of the DNA sequences of the cell and/or in a region affecting the expression of a gene. More particularly, said modification(s) will generally affect the coding region or the region responsible for or involved in the expression of one or more genes whose expression products are enzymes involved in mannosylation.

The reduced capacity of the fungal cells of the invention to mannosylate proteins may therefore result from the production of inactive enzymes due to structural and/or conformational changes, from the production of enzymes having altered biological properties, from the absence of production of said enzymes, or from the production of said enzymes at low levels.

The fungal cell mannosylation pathway involves attachment of a first mannosyl residue to the hydroxyl group of seryl and/or threonyl amino acids of proteins or peptides, and then the extension to O-linked di- and oligosaccharides by subsequent addition of mannosyl residues. The first mannosyl residue is transferred from dolichol monophosphate mannose (Dol-P-Man) to the protein in the endoplasmic reticulum, and the additional mannosyl residues are transferred from GPD-Man in the golgi.

In a preferred embodiment of the invention, the modified fungal cells carry genetic modification(s) in at least one gene whose expression product is involved in the attachment of a mannosyl residue to the hydroxyl group of seryl or threonyl amino acids.

In a another preferred embodiment of the invention, the modified fungal cells carry genetic modifications in at least one gene whose expression product is involved in the transfer of a mannosyl residue from the Dol-P-Man precursor to the hydroxyl group of seryl or threonyl amino acids. Still more preferably, one of these genes is a PMT gene (eg PMT1, PMT2, PMT3, PMT4, PMT5, PMT6 or PMT7). Preferably the PMT gene is PMT1, PMT5 or PMT7.

WO 94/04687, incorporated herein by reference, describes the preparation of *S. cerevisiae* deficient in O-mannosylation activity. A *S. cerevisiae* cell deficient in O-mannosylation activity was prepared by gene disruption, by insertion of the URA3 gene into the HindIII restriction site of the PMT1 ORF. The resulting mutants were grown on YEPD (about pH6.95) or on minimal media+Ade, +Leu (about pH4.75, declining with yeast growth). Unexpectedly, we have found that the pHs of the growth media used in WO 94/04687 are not optimal for the large scale culture of PMT mutants to produce secreted albumin. We have found that a growth medium of pH6.0-6.8 is beneficial in terms of host cell integrity during large scale fermentation.

In addition to modifications in a gene involved in the attachment of mannosyl residues to the hydroxyl group of seryl or threonyl amino acids, fungal cells of the invention may also carry modifications in the genes involved in subsequent additions of mannosyl residues leading to di- or oligosaccharides, or in the synthesis of the mannosyl residues donor (Dol-P-Man).

Preferably, the fungal cell has a genetic modification within a PMT gene or a gene which affects the expression or product of a PMT gene. A gene which affects the expression of a PMT gene may, for example, affect mRNA transcript levels or PMT product levels.

The fungal cell of the sixth aspect of the present invention can be chosen from filamentous fungi and yeasts. Preferably, the cells are yeasts, for example a yeast of the genus *Saccharomyces* (eg *S. cerevisiae*), the genus *Kluyveromyces* (eg *K. lactis*) or the genus *Pichia* (eg *P. pastoris*).

Preferably, the fungal cell expressing the recombinant albumin coding sequence is cultured in a culture medium of at least 5,000 L, more preferably at least 7,500 L.

Preferably, the fungal cell expressing the recombinant albumin coding sequence is cultured in a culture medium which is maintained in the range of pH6.2-6.7, more preferably pH6.3-6.5. Preferably, the pH of the culture medium is maintained using a pH controller set at a pH between pH6.3 and pH6.5, preferably at a pH: between 6.35 and 6.45 and more preferably at about pH6.4. Preferably, the pH controller is controlled within 0.20 or 0.10 pH units of any pH value within any one of the aforementioned pH ranges or within 0.20 or 0.10 pH units of pH6.4.

In an alternative embodiment, the fungal cell is cultured in a culture medium which is maintained in the range of pH5.30-pH5.90, preferably pH5.50-pH5.90, pH5.40-pH5.90 or pH5.40-5.60. Preferably, the lower control set point is between pH5.40 and pH5.60, preferably between pH5.45 and pH5.55, and preferably the lower control set point is about pH5.50.

The present invention provides processes for the preparation of highly purified albumin. The albumin is characterised by extremely low levels of colorants. The term "colorant" as used herein means any compound which colours albumin. For example, a pigment is a colorant which arises from the organism, such as yeast, which is used to prepare recombinant albumin, whereas a dye is a colorant which arises from chromatographic steps to purify the albumin.

The albumin is also characterised by extremely low levels of, or by being essentially free of; aluminium, lactate, citrate, metals, non-albumin human proteins, such as immunoglobulins, pre-kallikrein activator, transferrin, ⨍-acid glycoprotein, haemoglobin and blood clotting factors, prokaryotic proteins, fragments of albumin, albumin aggregates or polymers, or endotoxin, billirubin, haem, yeast proteins, animal proteins and viruses. By essentially free is meant below detectable levels.

The albumin of the invention may be at least 99.5% monomeric and dimeric, preferably essentially 100% monomeric and dimeric. Up to 0.5%, preferably 0.2% trimer is tolerable but larger forms of albumin are generally absent. It may be further characterised by one or more of the following characteristics. It has a nickel ion level of less than 100 ng, based on one gram of albumin; a glycation level of less than 0.6, preferably less than 0.10, 0.075 or 0.05 moles hexose/mole protein as measured in the Amadori product assay; an intact, i.e. homogeneous, C-terminus; a content of conA-binding albumin of less than 0.5% (w/w), preferably less than 0.2% or 0.15%; a free thiol content of at least 0.85 mole SH/mole protein; and substantially no C18 or C20 fatty acids. At least 99%, preferably at least 99.9%, by weight of the protein in the albumin preparations purified by the process of the invention is albumin. Such highly pure albumin is less likely to cause adverse side effects.

rHA purified according to the invention will generally be totally free of serum-derived contaminants, since none are present in the starting material.

In accordance with the present invention, highly pure albumin is obtained from an impure albumin solution. The process comprises one or more of the following steps: culturing in a fermentation medium a micro-organism transformed with a nucleotide sequence encoding the amino acid sequence of human albumin; preferably separating the micro-organism from the fermentation medium; conditioning the medium, if necessary, for further purification; passing the conditioned medium through three successive chromatography steps; ultrafiltering/diafiltering the product; passing the ultrafiltered product through a further chromatography step; ultrafiltering/diafiltering again before purification through two further chromatographic steps; and final ultrafiltration/diafiltration.

Alternatively, instead of the fermentation medium, the impure albumin solution may be a solution obtained from serum by any of the plethora of extraction and purification techniques developed over the last 50 years, for example those disclosed in Stoltz et al (1991) *Pharmaceut. Tech, Int.* June 1991, 60-65 and More & Harvey (1991) in "Blood Separation and Plasma Fractionation" Ed. Harris, Wiley-Liss, 261-306.

In a further alternative, the albumin may be obtained from a transgenic animal, such as goat, sheep or cattle, from, for instance, the milk or the blood of the animal or, in the case of transgenic chicken, from the egg white.

In a still further alternative, the albumin may be obtained from a transgenic plant, such as tobacco, potato or corn (maize).

In instances where the albumin is purified from non-plasma sources, prior art purification processes lead to a relatively high level of nickel ions. Albumin is known to have high affinity binding sites for copper, nickel and zinc ions at the N-terminus of the molecule. Consequently, the albumin molecule effectively concentrates nickel ions from the media used for cultivation and/or purification. Albumin purified according to this invention has a surprisingly low level of nickel ions.

Preceding or following any of the procedures of the present invention the albumin solution may undergo buffer exchange, concentration, dilution, heating (including sterilisation), cooling or may have salts etc. added to the albumin solution which may, for example, condition or adjust the pH of the solution. Optionally, the albumin may be treated with a reducing agent or may undergo a decolouration step.

The final product may be formulated to give it added stability and may be formulated according to its intended utility, eg it may be formulated for parenteral administration, preferably parenteral administration to a human. Suitably, the albumin undergoes sterilisation.

Preferably, the highly pure albumin product of the invention contains at least 100 g, more preferably 1 kg or 10 kg of albumin, which may be split between a plurality of vials.

The albumin of the present invention may be fulfil various roles in addition to therapeutic use in the treatment of burns, shock or blood loss. By way of example, it may be used as a final product excipient (e.g. in liquid formulations, freeze-dried formulations or formulations for inhalation), for stabilisation of other proteins during purification, in cell culture, viral production, gene therapy, in vitro fertilisation media, and for coating medical devices such as cannulae, catheters and vascular prostheses.

It should be appreciated that each aspect of the invention may be combined with one or more other aspects of the invention.

BRIEF DESCRIPTION OF THE DRAWINGS

The invention is further illustrated in the appended drawings in which:

FIG. 10 (SEQ ID NO. 1) and 11 (SEQ ID NO. 2) represent two DNA sequences with homology to the protein encoding region *Saccharomyces cerevisiae* PMT1.

FIG. 12 (SEQ ID NO. 3), FIG. 13 (SEQ ID NO. 4), FIG. 14 (SEQ ID NO. 5), and FIG. 15 (SEQ ID NO. 6) represent four DNA sequences with homology to the protein encoding region *Saccharomyces cerevisiae* PMT7.

FIG. 16 (SEQ ID NO. 7) and FIG. 17 (SEQ ID NO. 8) represent two DNA sequences with homology to the protein encoding region *Saccharomyces cerevisiae* PMT5.

DETAILED DESCRIPTION OF PREFERRED EMBODIMENTS OF THE INVENTION

Figure 1:
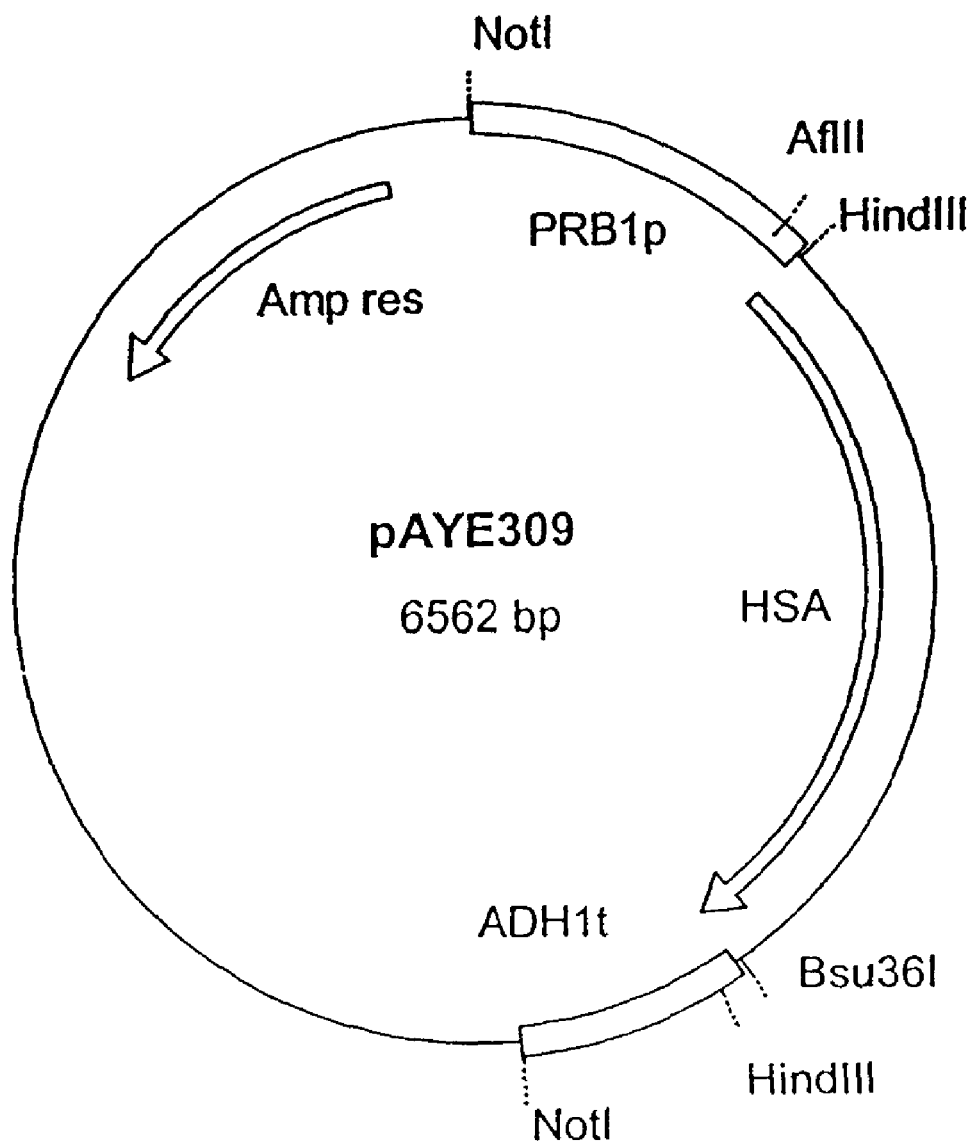
FIGS. 1 to 7 respectively show the construction of plasmids pAYE309, pAYE440, pAYE43S, pDB2241, pDB2242, pDB2243 and pDB2244.

Whereas the processes of the present invention can be utilised to obtain highly purified albumin from an impure albumin solution from a number of sources, such as serum, it is particularly applicable to purifying recombinant human albumin (rHA). The albumin produced in accordance with the invention may be any mammalian albumin, such as rat, bovine or ovine albumin, but is preferably human albumin.

DNA encoding albumin may be expressed in a suitable host to produce albumin. Thus, DNA may be used in accordance with known techniques, appropriately modified in view of the teachings contained herein, to construct an expression vector, which is then used to transform an appropriate host cell for the expression and production of albumin.

The DNA encoding the albumin may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. It is beneficial to incorporate more than one DNA sequence encoding a translational stop codon, such as UAA, UAG or UGA, in order to minimise translational readthrough and thus avoid the production of elongated, non-natural fusion proteins. A DNA sequence encoding the translation stop codon UAA is preferred. The vector is then introduced into the host through standard techniques, followed by selection for transformed host cells. Host cells so transformed are then cultured for a sufficient time and under appropriate conditions known to those skilled in the art, and in view of the teachings disclosed herein, to permit the expression of the albumin, which can then be recovered.

Many expression systems are known, including bacteria (for example *E. coli* and *Bacillus subtilis*), yeasts (for example *Saccharomyces cerevisiae*, *Pichia pastoris* and *Kluyveromyces lactis*), filamentous fungi (for example *Aspergillus*), plant cells, animal cells and insect cells. The preferred micro-organisms are the yeasts *Saccharomyces cerevisiae*, *Kluyveromyces lactis* and *Pichia pastoris*. It is particularly advantageous to use a yeast deficient in one or more protein mannosyl transferases involved in O-glycosylation of proteins, for instance by disruption of the gene coding sequence.

The albumin protein sequence does not contain any sites for N-linked glycosylation and has not been reported to be modified, in nature, by O-linked glycosylation. However, it has been found that rHA produced in a number of yeast species can be modified by O-linked glycosylation, generally involving mannose. The mannosylated albumin is able to bind to the lectin Concanavalin A. The amount of mannosylated albumin produced by the yeast can be reduced by using a yeast strain deficient in one or more of the PMT genes (WO 94/04687).

The most convenient way of achieving this is to create a yeast which has a defect in its genome such that a reduced level of one of the Pmt proteins is produced. For example, there may be a deletion, insertion or transposition in the coding sequence or the regulatory regions (or in another gene regulating the expression of one of the PMT genes) such that little or no Pmt protein is produced. Alternatively, the yeast could be transformed to produce an anti-Pmt agent, such as an anti-Pmt antibody.

To modify one of the PMT genes so that a reduced level of Pmt protein is produced, site-directed mutagenesis or other known techniques can be employed to create single or multiple mutations, such as replacements, insertions, deletions, and transpositions, as described in Botstein and Shortle. "Strategies and Applications of In Vitro Mutagenesis", *Science*, 229: 193-210 (1985), which is incorporated herein by reference. Suitable mutations include chain termination mutations (clearly stop codons introduced near the 3' end might have insufficient effect on the gene product to be of benefit; the person skilled in the art will readily be able to create a mutation in, say, the 5' three quarters of the coding sequence), point mutations that alter the reading frame, small to large deletions of coding sequence, mutations in the promoter or terminator that affect gene expression and mutations that de-stabilise the mRNA. Specific mutations can be introduced by an extension of the gene disruption technique known as gene transplacement (Winston, F. et al (1983) *Methods Enzymol.* 101, 211-228).

Generally, one uses a selectable marker to disrupt a gene sequence, but this need not be the case, particularly if one can detect the disruption event phenotypically. In many instances the insertion of the intervening sequence will is be such that a stop codon is present in frame with the Pmt sequence and the inserted coding sequence is not translated. Alternatively, the inserted sequence may be in a different reading frame to Pmt.

The gene may have one or more portions (optionally including regulatory regions, up to the whole gene) excised or inverted, or it may have a portion inserted, in order to result in reduced production of protein from one of the PMT loci and/or in the production of protein from one of the PMT loci having a reduced level of activity.

The PMT genes of *Saccharomyces cerevisiae* encode a family of seven (PMT1-PMT7) protein O-mannosyltransferases which vary in their specificity. These proteins are also known as dolichol phosphate-D-mannose: protein transferases, dolichyl-phosphate-D-mannose: protein O-D-mannosyltransferases or phosphomannose transferases (Gentzsch and Tanner, EMBO 15, 5752-5757, 1996, and references included therein). This family of integral membrane enzymes catalyses the transfer of mannose, in the form of dolichyl phosphate mannose, onto the hydroxyl group of serine or threonine within the polypeptide chain, described by the following reaction:

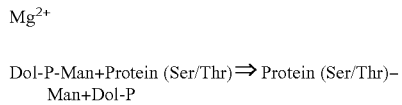

Dol-P-Man+Protein (Ser/Thr) ⇒ Protein (Ser/Thr)–Man+Dol-P

The available evidence suggests that the synthesis of dolichyl phosphate mannose and the subsequent transfer of mannose to the protein occurs in the endoplasmic reticulum.

It is clear that the enzymes of this family have different substrate (protein) no specificities (Gentzsch and Tanner (1997) *Glycobiology* 7, 481-486). Five of seven test proteins were substrates for Pmt1p and Pmt2p, the products of the PMT1 and PMT2 genes respectively, as shown by their underglycosylation in pmt1 or pmt2 mutant *Saccharomyces cerevisiae* strains. Another two test proteins were apparently unaffected by either PMT1 or PMT2 mutations, but were underglycosylated in pmt4 mutant strain.

The 92 kD Pmt1p protein O-mannosyltransferase enzyme has been purified to homogeneity from solubilised *Saccharomyces cerevisiae* membranes (Strahl-Bolsinger and Tarner (1991) *Eur. J. Biochem.* 196, 185-190). The gene encoding, for the Pmt1p (PMT1) has been cloned and sequenced. The gene is located on chromosome IV and encodes a single polypeptide with a primary sequence of 817 amino acids (Strahl-Bolsinger et al (1993) *P.N.A.S. USA* 90, 8164-8168). The sequence information of PMT1 (and other PMT genes) may be used for the identification of related mannosyltransferases encoding genes in *Saccharomyces cerevisiae*.

The sequences shown in FIGS. 10 and 11 are homologous with the protein encoding region *Saccharomyces cerevisiae* PMT1, the sequences shown in FIGS. 12 to 15 are homologous with the protein encoding region *Saccharomyces cerevisiae* PMT7 and the sequences shown in FIGS. 16 to 17 are homologous with the protein encoding region *Saccharomyces cerevisiae* PMT5 Persons skilled in the art will appreciate that any one of these sequences may be used to identify (or disrupt) a *Saccharomyces cerevisiae* mannosyltransferase gene. It will be appreciated that fragments of the sequences represented in FIGS. 10 to 17 may similarly be used, as may sequences which are homologous with the sequences represented in FIGS. 10 to 17 and the fragments thereof. Techniques for generating homologous sequences are well known in the art.

It should be appreciated that by a homologous sequence, we include sequences having at least 70%, 80%, 90%, 95%, or 98% homology with a sequence shown in any one of FIGS. 10 to 17, or with a fragment of a sequence shown in any one of FIGS. 10 to 17.

Percent homology can be determined by, for example, by comparing sequence information using the GAP computer program, version 6.0 described by Devereux et al. (*Nucl. Acids res.* 12:387, 1984) and available from the University of Wisconsin Genetics Computer Group (UWGCG). The GAP program utilises the alignment method of Neddleman and Wunsch (*J. Mol. Biol.* 48:443, 1970), as revised by Smith and Waterman (*Adv. Appl. Math* 2.482. 1981). The preferred default parameters for the GAP program include: (1) a unary comparison matrix (containing a value of 1 for identities and 0 for non-identities) for nucleotides, and the weighted comparison matrix of Bribskov and Burgess, *Nucl. Acids Res.* 14:6745, 1986 as described by Schwarts and Dayhoff, eds, *Atlas of Protein Sequence and Structure, National Biomedical Research Foundation*, pp 353-358, 1979; (2) a penalty of 3.0 for each gap and an additional 0.10 penalty for each symbol in each gap; and (3) no penalty for end gaps.

If a yeast other than *S. cerevisiae* is used, disruption of one or more of the genes equivalent to the PMT genes of *S. cerevisiae* is also beneficial, eg in *Pichia pastoris* or *Kluyveromyces lactis*. The sequence of PMT1 (or any other PMT gene) isolated from *S. cerevisiae* may be used for the identification or disruption of genes encoding similar enzymatic activities in other fungal species. The cloning of the PMT1 homolog of *Kluyveromyces lactis* is described in WO 94/04687.

If a yeast other than *S. cerevisiae* is used, the sequences represented in FIGS. 10 to 17 may also be used to identify (or disrupt) a gene equivalent to a *S. cerevisiae* PMT gene. Persons skilled in the art will appreciate that fragments of the sequences represented in FIGS. 10 to 17 may similarly be used, as may sequences which are homologous with the sequences represented in FIGS. 10 to 17 and the fragments thereof.

Methods for carrying out gene disruptions are described in the literature, an example of which is described by Boehm et al. (Boehm, T., Pirie-Shepherd, S., Trinh, L., Shiloach, J. and Folkman, J. 1999) *Yeast* 15 563-572) which describes the use of the *Saccharomyces cerevisiae* SUC2 gene as a marker Ranked by *Pichia pastoris* DNA specific to the target gene. In the example of *Pichia pastoris* disruption, the SUC2 DNA sequence could be inserted at a position within any of the DNA sequences represented in FIGS. 10 to 17.

The yeast will advantageously have a deletion of the HSP150 and/or YAP3 genes as taught respectively in WO 95/33833 and WO 95/23857.

In a preferred embodiment the yeast is transformed with an expression plasmid based on the *Saccharomyces cerevisiae* 2 μm plasmid. At the time of transforming the yeast, the plasmid contains bacterial replication and selection sequences, which are excised, following transformation, by an internal recombination event in accordance with the teaching of EP 286 424. The plasmid also contains an expression cassette comprising: a yeast promoter (eg the *Saccharomyces cerevisiae* PRB1 promoter), as taught in EP 431 880; a sequence encoding a secretion leader which, for example, comprises most of the natural HSA secretion leader, plus a small portion of the *S. cerevisiae* α-mating factor secretion leader as taught in WO 90/01.063; the HSA coding sequence, obtainable by known methods for isolating cDNA corresponding to human genes, and also disclosed in, for example, EP 73 646 and EP 286 424; and a transcription terminator, preferably the terminator from *Saccharomyces* ADH1, as taught in EP 60 057. Preferably, the vector incorporates at least two translation stop codons.

The choice of various elements of the plasmid described above is not thought to be directly relevant to the purity of the albumin product obtained, although the elements may contribute to an improved yield of product. A preferred embodiment of the fermentation and purification process is described in Example 1.

EXAMPLE 1

The cloning strategy for construction of the albumin-producing micro-organism was as disclosed in EP 431 880 except that the 3' end of the albumin coding sequences and its junction with the ADH1 transcription termination sequence were altered such that the ADH coding sequence was eliminated and such that two consecutive in-frame translation stop codons were present, followed by a third stop codon downstream, as follows:

```
                                              SEQ ID NO. 9
 . . . L    G    L    stop stop A    stop
 . . . TTA  GGC  TTA  TAA  TAA  GCT  TAA . . .
```

This was achieved by modification of the ADH1 terminator from plasmid pAYE309, described in EP 431 880, by PCR mutagenesis using two single stranded oligonucleotides, JMADH1 and JMADH2 with the sequences:

```
JMADH1
                                            SEQ ID NO. 10
       HindIII
5'-GCATAAGCTTTGGACTTCTTCGCCAGAGGTTTGGTCAAG-3'

JMADH2
                                            SEQ ID NO. 11
                                  NotI    BamHI
3'-TGGACAACATTAGCAAGAAGGTGTGCCTAGCGCCGGCGCCTAGGTA
CG-5'
```

Figure 2:
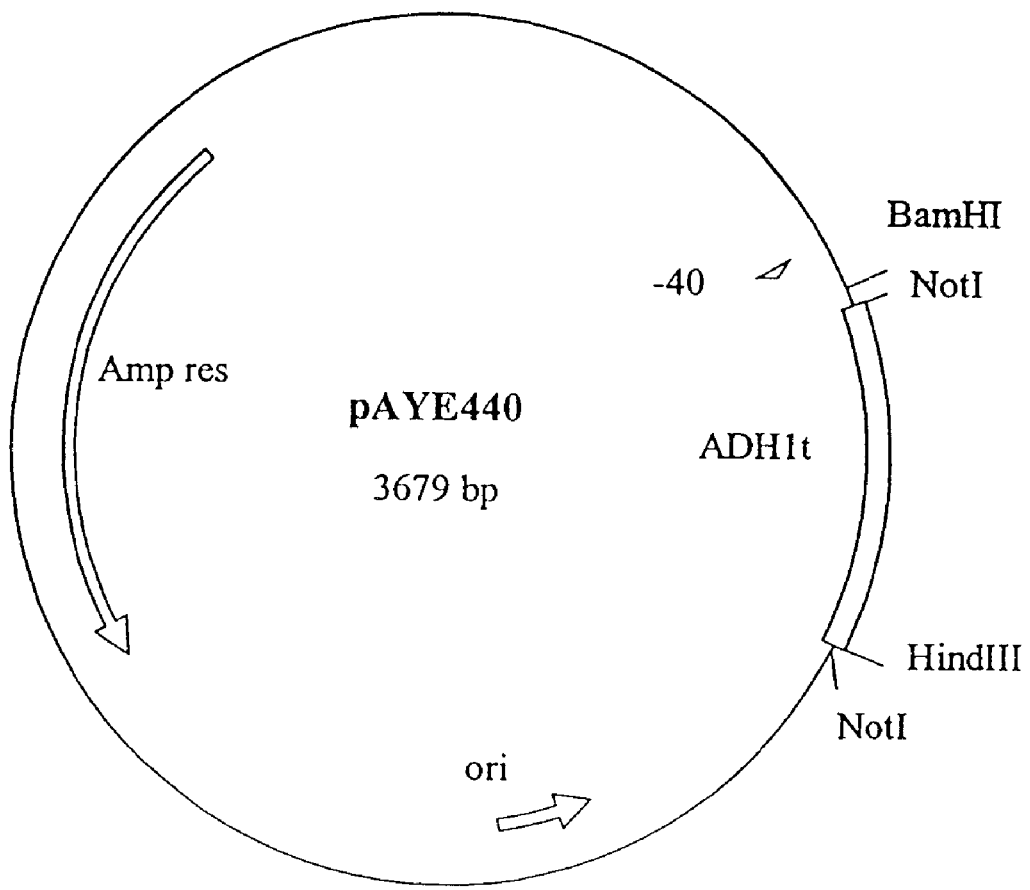

The PCR conditions were 25 cycles of 94° C. for 60 seconds, 37° C. for 120 seconds and 72° C. for 180 seconds. The 0.48 kb PCR product was digested with both HindIII and BamHI and ligated into plasmid pBST+, described in WO 97/24445, similarly digested with HindIII and BamHI, to create plasmid pAYE440 (FIG. 2). The ADH1 terminator was further modified by PCR mutagenesis using two single stranded oligonucleotides, AT19R and the universal −40 primer with the sequences:

```
      AT19R
                                            SEQ ID NO. 12
            HindIII
      5'-AGTCCAAGCTTAATTCTTATGATTTATGAT-3'

-40
                                            SEQ ID NO. 13
      3'-CAGCACTGACCCTTTTG-5'.
```

Figure 3:
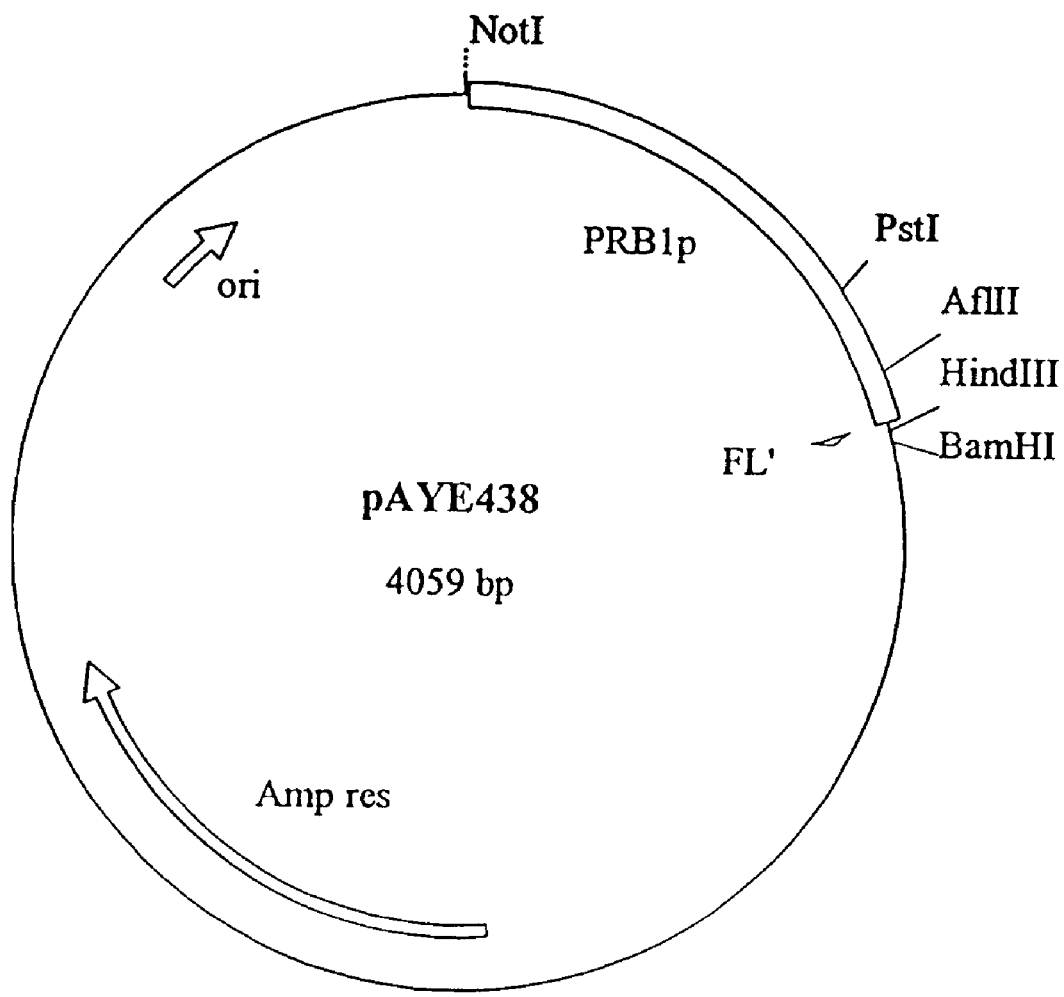
Figure 4:
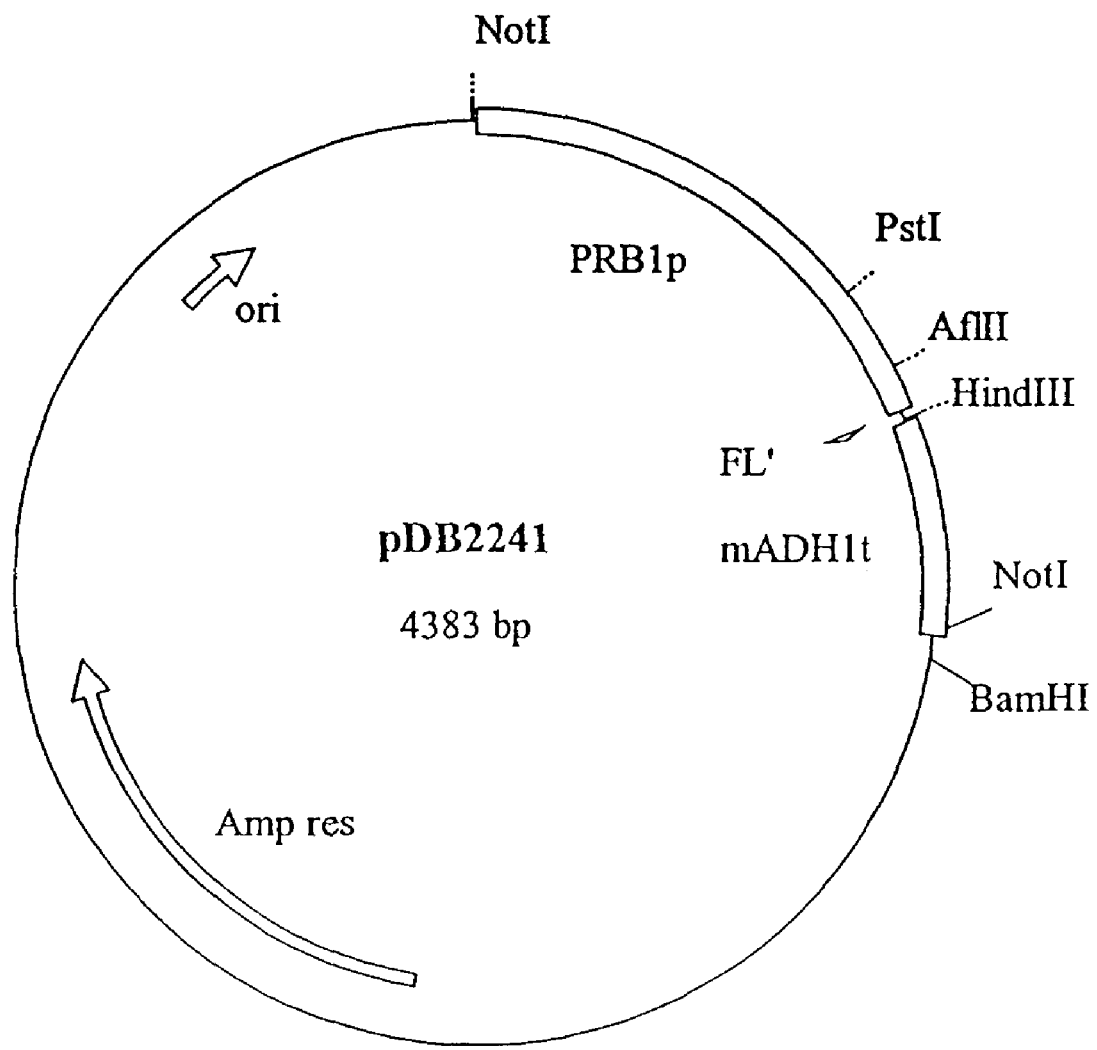

The PCR conditions were 25 cycles of 94° C. for 30 seconds, 50° C. for 40 seconds and 72° C. for 50 seconds and then one cycle of 72° C. for 10 minutes, using the ADH1 terminator in pAYE440 as a template (FIG. 2). The machine used was a Perkin Elmer GeneAmp PCR System 9600. A product of the correct size, approximately 0.33 kb, was obtained and digested with both HindIII and BamHI. Plasmid pAYE309, described in EP 431 880, was digested with NotI and HindIII and the 0.84 kb DNA fragment containing the PRBI promoter fragment and part of the HSA/MFα-1 leader sequence (WO 90/01063) employed to direct secretion of mature HSA, was ligated into NotI and HindIII digested pBST+, described in WO 97/24445, to generate plasmid pAYE438 (FIG. 3). The recipient plasmid pAYE438 was digested with HindIII and BamHI and the modified ADH1 terminator was successfully cloned into this vector to generate plasmid pDB2241 (FIG. 4). This plasmid contains the pBST+ (WO 97/24445) backbone, the PAB1 promoter and the modified ADH1 terminator.

To facilitate the introduction of two translation stop codons at the end of the HSA coding region and create the required HindIII site, the 3N end of the HSA coding region was altered.

Figure 5:
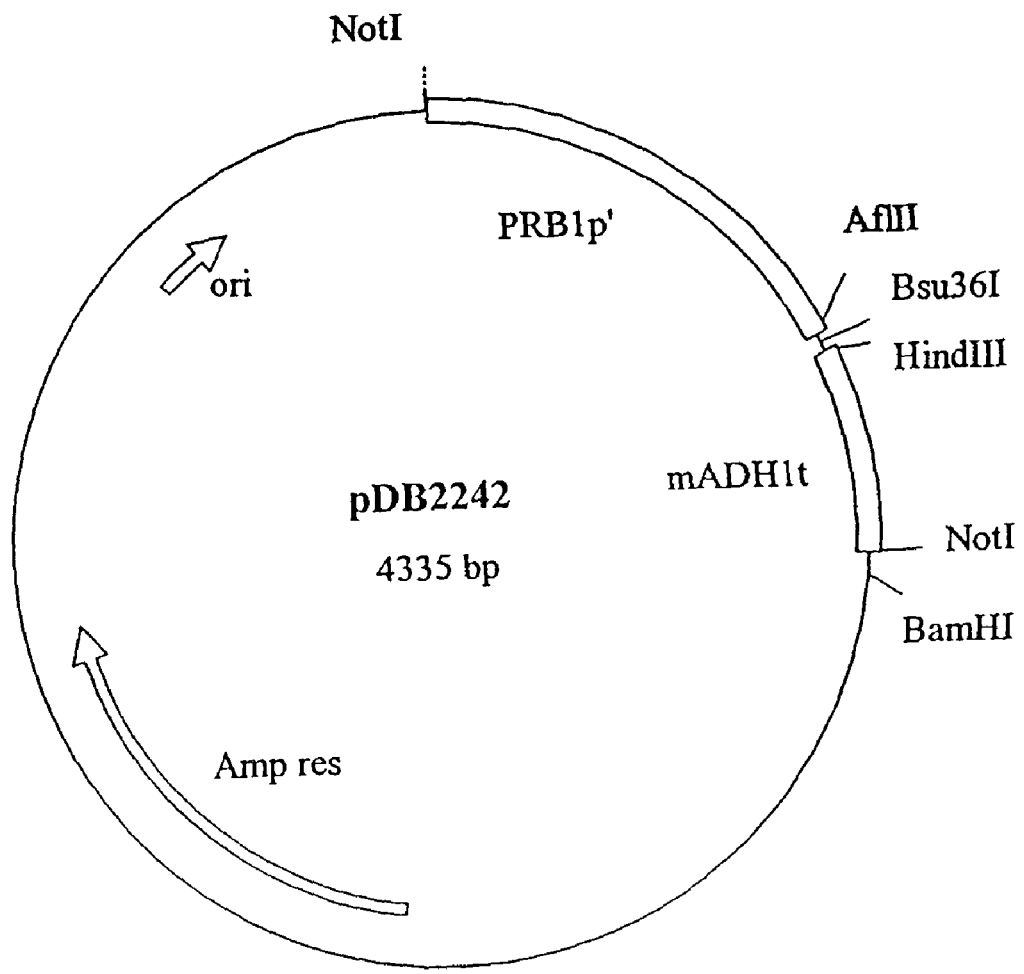

The double stranded oligonucleotide linker, AT21/AT22 was ligated into AflII/HindIII cut pDB2241 and comprised an AflII site at its 5N end, a stuffer region and then the Bsu36I to HindIII sequence of the HSA coding DNA, but with the addition of an extra DNA translation stop codon. Clones with the linker inserted were checked by DNA sequencing and the correct plasmid designated pDB2242 (FIG. 5).

```
Linker AT21/22
AT21
                                            SEQ ID NO. 14
AflII            Bsu36I              HindIII SEQ ID NO. 15
TTA AGA GTC CAA GCC TTA GGC TTA TAA TA
   CT CAG GTT CGG AAT CCG AAT ATT ATTCGA SEQ ID NO. 16
           A L G L Stop Stop
```

Figure 6:
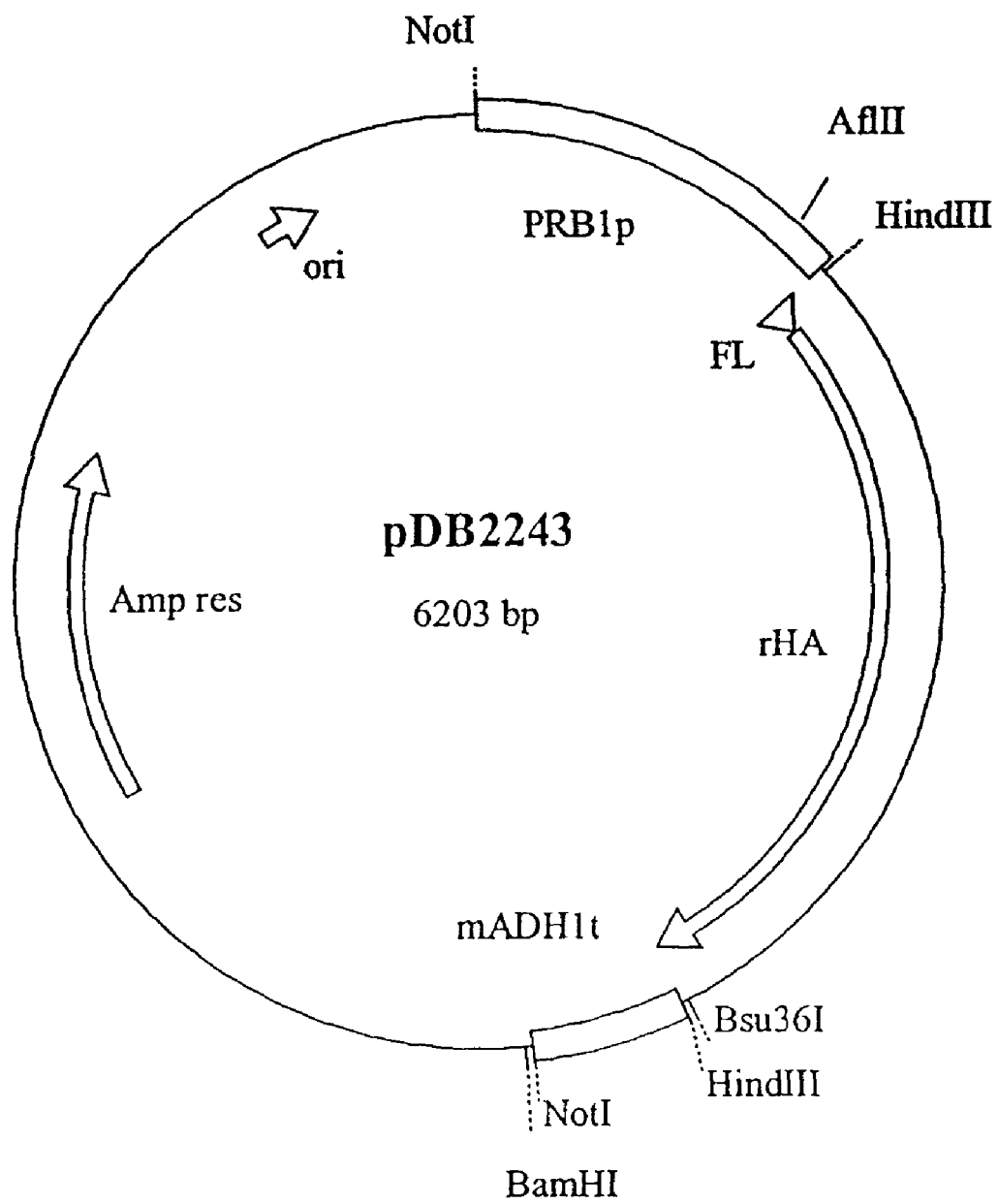
Figure 7:
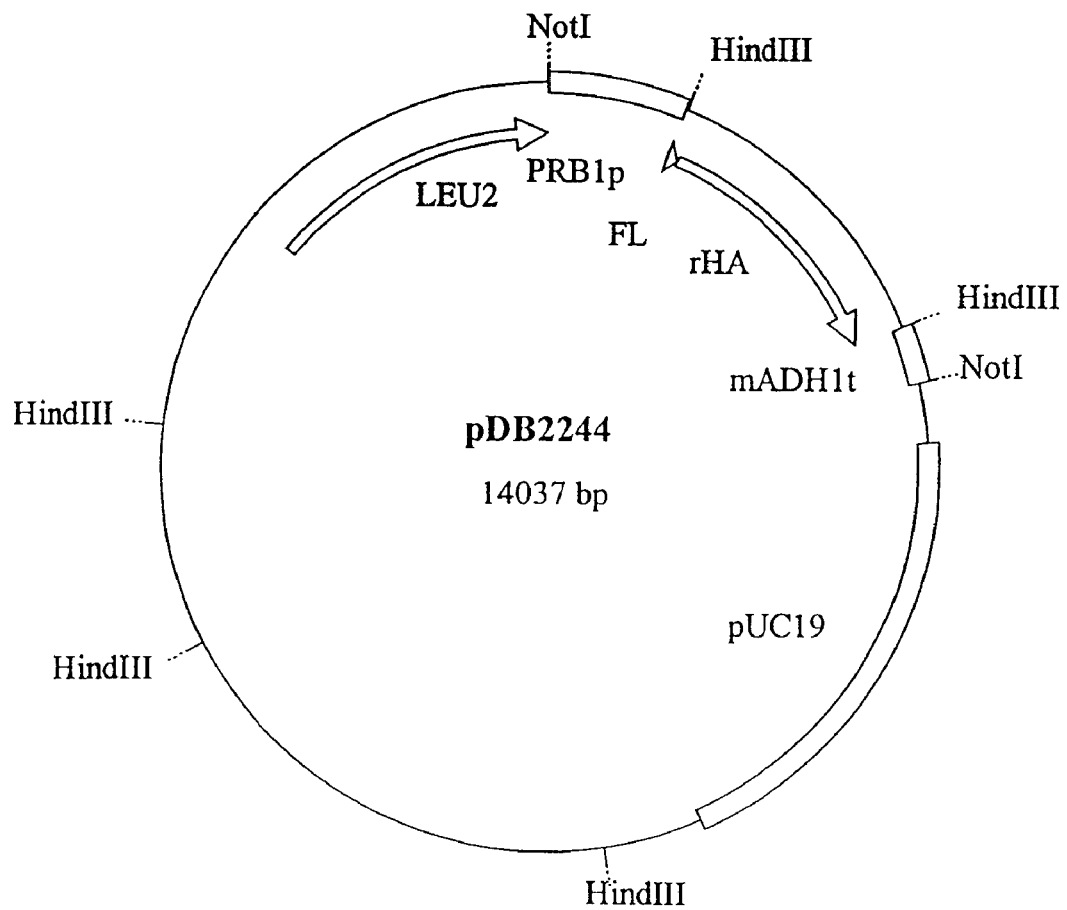

To create the final rHA expression cassette the AflII/Bsu36I fragment of pAYE309 (FIG. 1) was ligated into AflII/Bsu36I digested pDB2242, making plasmid pDB2243 (FIG. 6). Finally, the rHA expression disintegration vector was made by ligating the NotI expression cassette from pDB2243 into NotI cut pSAC35 (Sleep et al, 1991, Bio/Technology 9, 183-187 and EP 431 880) to generate the plasmid pDB2244 (FIG. 7) in which the direction of rHA transcription is in the same orientation as that of the LEU2 gene.

The plasmid pDB2244 is therefore derived from the disintegration vector pSAC3 (Chinery and Hinchliffe (1989) *Current Genetics* 16, 21-25) and comprises the whole of the 2 μm plasmid, the LEU2 gene to complement the host leu2 mutations, the expression cassette in which the PRB1 promoter drives expression of the HSA sequence and the bacterial plasmid pUC9. The latter is excised from the plasmid by the *S. cerevisiae* 2 μm FLP recombinase system such that no bacterial DNA is present in the organism used for production of rHA (Chinery and Hinchliffe, op cit.).

The expression vector utilises the *S. cerevisiae* PRB1 promoter and ADH1 transcription terminator to control expression and the HSA/MFα-1 leader sequence (WO 90/01063) to direct secretion of mature HSA.

The plasmid pDB2244 was introduced into a *Saccharomyces cerevisiae* strain which was leu2, yap3, hsp150, pmt1 [cir°] by the method described by Hinnen et al, (1978) P.N.A.S. 75, 1929. The pmt1 mutation may be achieved by the method of WO 94/04687. Transformants were selected on a buffered minimal medium (0.15% (w/v) yeast nitrogen base without amino acids and ammonium sulphate (Difco), 0.5%

(w/v) ammonium sulphate, 0.1 M citric acid/Na$_2$HPO$_4$.12H$_2$O pH6.5, 2% (w/v) sucrose)) lacking leucine. When transformants were grown for 72 hours at 30° C., 200 rpm in 50 ml flasks containing either 10 ml of complex (YEP, 1% (w/v) yeast extract, 2% (w/v) bactopeptone and 2% (w/v) sucrose), or buffered minimal medium liquid medium, rHA could be detected in the cell free culture supernatant by SDS-polyacrylamide gel electrophoresis and/or by rocket gel immunoelectrophoresis.

A stock master cell culture in buffered minimal medium is used to prepare running stocks (working cell bank) of process yeast suitable for the preparation of shake flask cultures by freezing aliquots of the culture in the presence of 20% (w/v) trehalose.

The fermentation was essentially the same as is described in WO 96/37515 and U.S. Pat. No. 5,728,553, both of which are incorporated herein by reference, except for the following differences:

Seed Fermentation

After the medium for rHA production has been added to the seed fermenter vessel, the operating temperature of 30° C. is set, as well as the minimum stirrer speed set to achieve homogeneity and so avoid gradients of nutrients such as oxygen or carbon. The initial pH is adjusted with ammonia solution (specific gravity 0.901) using a pH controller set at 6.40; controlled at 6.40±0.10.

Alternatively, pH is maintained in the range of 5.50 to 5.90, with the lower control set point being 5.50. The initial pH may be adjusted with ammonia (eg aqueous ammonia specific gravity 0.880). This lower fermentation pH results in an enhanced mass spectrometry profile of the rHA.

It is preferable for the initial pH to be near the top of the aforementioned ranges to facilitate observation of early metabolism, since a decline in pH is the first sign of growth detectable by on-line instruments.

Particularly for strains with a deficiency in one or more of the PMT genes, it has been found to be beneficial for the fermentation to be conducted at a higher pH than is normally required. Thus, rather than control the pH at approximately 5.5, it is beneficial to have a control set point between pH6.20 and pH6.70, preferably between pH6.3 and 6.5. At such a higher pH, the quality of the centrate is significantly improved due to reduced cell lysis. Cell lysis results in cell debris remaining in suspension following a centrifugation step of the fermentation which is sufficient only to remove all whole cells from the supernatant. This is demonstrated in Table 1, where a significant reduction in the wet weight content of a culture supernatant is shown when the yeast is cultured in the pH range 6.3 to 6.5 compared to pH5.5.

TABLE 1

Relationship between centrate quality and fermentation pH in seed fermenter vessel.

| Fermentation pH | Wet Weight Content of Supernatant (g · L$^{-1}$) |
|---|---|
| 5.5 | 9.9 |
|  | (2.4, 6) |
| 6.3-6.5 | 3.4 |
|  | (1.0, 13) |

Values in parentheses are standard deviation and number of samples.

2M H$_2$SO$_4$ is also used as a pH corrective agent. Sucrose to 20 g·L$^{-1}$, MW10 batch vitamins, and Breox FMT30 antifoam to 0.04 g·L$^{-1}$ are added to the vessel.

Sterile filtered air is introduced into the vessel at 0.5 v/v/m (ie 0.5 liter non-compressed air per liter of medium per minute), the medium is inoculated to >10 mg cell dry weight L$^{-1}$ from axenic shake flask culture and a supervisory computer control system is initiated. The expected batch phase is 62±10 h from an inoculum concentration of 12 mg·L$^{-1}$. MW10 feed must be connected before the end of the batch phase (volume equal to batch volume).

Features of the fermentation control algorithm include: the end of batch phase being signalled by dissolved oxygen tension (DOT) increase of >15% in 30 min; the feed being initiated at 0.05 ml per liter batch medium; the substrate feed rate being determined according to the formula, $SF=SF_o e k^{\mu k}$, wherein SF is substrate feed rate (mL·min$^{-1}$); $SF_0$ is initial substrate feed rate (mL·min$^{-1}$), μ is specific growth rate (for example 0.06 h$^{-1}$), and k is a counter variable started at 0 and increased by 0.0167 once every 1 min if all conditions are met.; and the substrate feed rate (via manipulation of k) being reduced in response to DOT<15% and/or respiratory quotient (RQ)≧1.2.

The feed is stopped if the pH<6.2 or if the temperature<29.0° C. or >31.0° C. This may also be done automatically through the control algorithm. The SF is no reduced if the average RQ>1.13 over a 2 h period, or if there is evidence of ethanol or acetate accumulation.

Agitation is increased to maintain DOT>20% air saturation. Once the feed is started, the concentration of Breox FMT30 is increased to 0.3 g·L$^{-1}$ (calculated on final volume). The expected feed phase duration is 65±17 h, dependent upon transfer limitations of the vessel.

The air flow is increased through the fermentation to maintain the values of oxygen uptake rate (OUR) and carbon dioxide evolution rate (CER), at levels sufficient to provide accurate gas analysis. The air flow rate of the fermentation is nominally 1 v/v/m, Daily checks are performed to determine purity of culture and CDW. Appropriate samples are retained. At the end of the feed, the culture is transferred to a production vessel.

Production Fermentation

The production fermenter is inoculated at 0.25-1.00 g·cdw·L$^{-1}$. The initial pH is adjusted with ammonia solution (SG 0.901) using a pH controller set at pH6.40; so controlled at 6.40±0.10.

Alternatively, pH is maintained in the range of 5.50 to 5.90, with the lower control set point being 5.50. The initial pH may be adjusted with ammonia (eg aqueous ammonia specific gravity 0.880). This lower fermenation pH results in an enhanced mass spectrometry profile of the rHA.

It is preferable for the initial pH to be near the top of the aforementioned ranges to facilitate observation of early metabolism, since a decline in pH is the first sign of growth detectable by on-line instruments.

Particularly for strains with a deficiency in one or more of the PMT genes, it has been found to be beneficial for the fermentation to be conducted at a higher pH than is normally required. Thus, rather than control the pH at approximately 5.5, it is beneficial to have a control set point between pH6.20 and pH6.70, preferably between pH6.3 and 6.5. At such a higher pH, the quality of the centrate is significantly improved due to reduced cell lysis. Cell lysis results in cell debris remaining in suspension following a centrifugation step of the fermentation which is sufficient only to remove all whole cells from the supernatant. This is demonstrated in Table 2, where a significant reduction in the wet weight content of a culture supernatant is shown when the yeast is cultured at pH 6.5 compared to pH 5.5.

TABLE 2

Relationship between centrate quality and fermentation pH in production vessel.

| Fermentation pH | Wet Weight Content of Supernatant (g · L$^{-1}$) |
| --- | --- |
| 5.5 | 36.3 |
| 6.5 | 4.7 |

2M H$_2$SO$_4$ is also used as a pH corrective agent. Sucrose to 20 g·L$^{-1}$, MW10 batch vitamins, and Breox FMT30 antifoam to 0.04 g·L$^{-1}$ are added to the vessel.

The initial substrate feed rate is determined according to the formula:

$$SF_o = \frac{1000 \times \mu \times [CDW] \times V_{batch}}{60 \times Y_{x/s} \times [sucrose]}$$

wherein SF$_0$ is initial substrate feed rate, μ is specific growth rate (for example 0.06 h$^{-1}$), V$_{batch}$ is batch volume (L), Y$_{x/s}$ is cell yield (g·L$^{-1}$), [sucrose] is sucrose concentration (g·L$^{-1}$) and [CDW] is cell dry weight concentration (g·L$^{-1}$). The substrate feed rate is determined according to the formula, SF$_0$e$^{\mu k}$, wherein SF is substrate feed rate (mL·min$^{-1}$); SF$_0$ is initial substrate feed rate (mL·min$^{-1}$), μ is specific growth rate (h$^{-1}$) (for example 0.06 h$^{-1}$), and k is a counter variable started at 0 and increased by 0.0167 once every 1 min if all conditions are met. A number of conditions are constantly reviewed during the fermentation, and used to adjust SF via manipulation of k; SF is reduced in response to DOT<15% and/or respiratory quotient (RQ)≧1.2. The feed is stopped if the pH<6.2 or if the temperature<29.0° C. or >31.0° C. This may also be done automatically through the control algorithm. The SF is reduced if the average RQ>1.13 over a 2 h period, or if there is evidence of ethanol or acetate accumulation.

Agitation increased to maintain DOT≧20% air saturation, and maintained at a maximum once attained in order to facilitate mixing. Once the feed is started and the culture is under carbon limitation, the concentration of Breox FMT30 is increased to 0.2-0.32 g·L$^{-1}$ (calculated on final volume). The expected feed phase duration is dependant upon transfer limitations of the vessel, typically 90-120 h at the 8,000 L scale.

The air flow is increased incrementally through the fermentation to maintain the values of oxygen uptake rate (OUR) and carbon dioxide evolution rate (CER), at levels sufficient to provide accurate gas analysis. The vessel is overpressured as necessary to enhance OTR. The air flow rate of the fermentation is nominally 1 v/v/m. Daily checks can be performed to determine purity of culture and CDW, and appropriate samples are retained.

The culture is held for downstream processing at the end of the feed.

Hold of Production Culture

The production culture may be held under appropriate conditions to enable batch processing of the culture. The hold time should be kept to a minimum, but can be extended up to 48 hours and beyond if necessary (eg to 5 days). It will be appreciated that, under conditions of batch processing, the constraints of hold time as expressed herein apply to the final portion of the culture to be processed.

The centrate from the fermentation, or an impure albumin solution from any other source (such as plasma), is prepared, or conditioned, for chromatography on a cation exchange matrix while protecting the rHA from polymerisation and protease activity. Preferably, sodium octanoate is added (Chromatography Solution 14 (CS14)—Table 3) to a final concentration of 1-10 mM, for example approximately 5 mM. The pH is adjusted with acetic acid to pH4.3-4.8, preferably 4.50±0.1 (most preferably ±0.05) and the conductivity is checked to be <5.5 mScm$^{-1}$.

Chromatograhy

All operations can be carried out at ambient temperature (20±5° C.). The albumin loads (g/L) for the chromatography columns are determined from titres of albumin (g/L) by either SDS-PAGE (at the first step) or GP-HPLC (for all other columns). The progress of each step is monitored by measuring UV absorbance on line, for example at 254 or 280 nm.

In a particularly preferred embodiment of the present invention the purification process comprises the following steps: cation exchange chromatography (SP-FF); anion exchange chromatography (DE-FF); affinity chromatography (DBA); ultrafiltration and diafiltration; a second affinity chromatography step (PBA); ultrafiltration and diafiltration; a second cation exchange chromatography step (SP-FF2); and a second anion exchange chromatography step (DE-FF2). Preferably, these purification processes are followed by final ultrafiltration/diafiltration followed by a formulation step, and/or placing of the solution into a final container.

The sequence of chromatographic steps as described here is novel and inventive in a number of aspects. The use of an aminophenylboronate (PBA) matrix with an improved buffer, as described herein, and a small load volume has been shown to give increased yeast antigen clearance, as measured by ELISA (about 4-20 fold). The buffer used with the aminophenylboronate matrix was unexpectedly found to be particularly beneficial, and it represents the result of intensive trials of a plethora of buffers of widely ranging constituents and properties. The buffer provides a significantly increased clearance of yeast antigens, when compared with the buffer used in the PBA chromatography step of WO 96/37515.

Loading the aminophenylboronate matrix with a highly concentrated albumin solution, for example 10±10 g·L$^{-1}$, means that improved resolution of the rHA and yeast antigens can be achieved because of the smaller load volume.

WO 96/37515 includes a S200 gel permeation step after a first affinity chromatography step. The gel filtration step purified the albumin with respect to yeast antigens, pigment and dimerised albumin. We have found that this step is no longer necessary because of the improvements we have made to the aminophenylboronate affinity step and the introduction of additional cation and anion exchange steps.

Following the aminophenylboronate affinity step it is preferred that the albumin is concentrated and diafiltered for a negative mode cation exchange step. We have found that the combination of this diafiltration step and cation exchange step substantially reduces the relative concentration of nickel ions. In particular, exposing rHA to a low pH is effective in reducing nickel ion levels. Consequently, albumin purified according to the present invention has a surprisingly low nickel ion content (less than 100 ng/g of albumin).

The negative mode cation exchange step, as described herein, is used to remove Concanavalin A binding material (cbm) which is a small amount of modified rHA, thought to be glycosylated. The negative mode cation exchange step has been found to reduce the cbm content produced by recombinant pmt1-mutant *Saccharomyces cerevisiae* by approximately 1.3-fold. A greater effect is achieved with rHA derived from non-pmt1 mutants (2-3 fold clearance).

In comparison with other commercial yeasts, *Saccharomyces cerevisiae* produces a relatively low level of modified rHA. Accordingly, the negative mode cation exchange step and the use of cells with a deficiency in one or more of the PMT genes may be of even greater importance if the rHA is produced by a recombinant host other than *Saccharomyces cerevisiae*.

The chromatography solutions used during the purification of albumin are detailed in Table 3. Because of the very large scale manufacture of albumin, and the relatively low cost of the product, these buffer salts are the most suitable for the process as they are available in a highly pure form at industrial scale and are low cost compared to other commonly used buffers such as Tris, HEPES or MOPS. Alternative buffers could be used in place of the ones used in Table 3, for example buffers of a similar $pK_a$ (eg malate for acetate), but in most instances cost and availability at large scale rule out their use. Alternative salt forms can be used provided they are soluble, available at industrial scale and low cost.

Chromatography can be performed using either axial flow columns, such as those available from Pharmacia, or using radial flow columns, such as those available from Sepragen. A fluidised bed may be used, at least for the first step.

The buffer solutions can be prepared at the concentrations described below, or concentrated stock solutions can be prepared and mixed or diluted on-line for immediate use.

Cation Exchange Chromatography

Albumin is concentrated and purified with respect to at least yeast proteins (if the albumin is rHA from a yeast fermentation) and other antigens, low molecular weight contaminants and pigmented compounds by cation exchange chromatography. The method uses a commercial cation exchange matrix such SP-Sepharose FF, SP-Spherosil, CM-Sepharose FF, CM-Cellulose, SE-Cellulose or S-Spherodex. Preferably, the matrix is SP-Sepharose FF (Pharmacia) which, if used in an axial flow column, may be at a bed height of 5 to 25 cm, preferably 10 to 15 cm, for example 12.5 cm. If a radial flow-type column is used, a suitable bed flow path length is 11.0±1.0 cm. A column loading of 10 to 50 g albumin/L, preferably 40±10 g albumin/L, of matrix is suitable. The matrix is equilibrated with a buffer to remove the alkali storage solution; preferably the buffer should be strong enough to reduce the pH to approximately pH6.0. A buffer such as CS01 is used to remove storage solution CS07 from the column; however, any buffer with a pH<6.0 could be used. Equilibration is Judged to be complete when the pH of the column effluent is approximately pH6.0.

TABLE 3

Chromatography solutions for the purification of albumin

| No. | Name | Constituent | Concentration $(g \cdot L^{-1})$ | pH | Conductivity $(mS \cdot cm^{-1})$ |
|---|---|---|---|---|---|
| CS01 | SP-FF Equilibrant/Wash 3/ DE-FF Equilibrant | $CH_3COOH$ NaOH (27% (w/w)) | 1.85 4.00 | 5.45-5.65 | 1.9-2.2 |
| CS02 | SP-FF Wash 1 | $CH_3COOH$ NaOH (27% (w/w)) | 3.00 1.19 | 3.9-4.1 | 0.6-0.8 |
| CS03 | SP-FF Wash 2 | $CH_3COOH$ NaOH (27% (w/w)) NaCl | 1.62 1.19 117 | 3.9-4.1 | 125-165 |
| CS04 | SP-FF Eluent/ DE-FF Pre-Equilibrant | $CH_3COOH$ NaOH (27% (w/w)) Octanoic Acid | 5.13 11.5 0.721 | 5.4-5.6 | 5.0-6.0 |
| CS05 | Salt Clean | NaCl Polysorbate 80 | 58.4 5.00 | 5-9 | 75-95 |
| CS06 | 0.5M NaOH | NaOH (27% (w/w)) | 74.1 | >12 | 80-120 |
| CS07 | 20 mM NaOH | NaOH (27% (w/w)) | 2.96 | >12 | 3.5-5.5 |
| CS08 | DE-FF Wash | $K_2B_4O_7 \cdot 4H_2O$ | 4.80 | 9.0-9.4 | 2.5-3.5 |
| CS09 | DE-FF Eluent | $K_2B_4O_7 \cdot 4H_2O$ | 33.6 | 9.2-9.5 | 15.0-18.0 |
| CS10 | DBA Equilibrant/Wash | $CH_3COONH_4$ NaOH (27% (w/w)) | 19.3 5.93 | 8.7-9.1 | 18-22 |
| CS11 | DBA Eluent | NaCl NaOH (27% (w/w)) $H_3PO_4$ (85%(w/w)) | 117 14.1 5.79 | 6.7-7.1 | 125-165 |
| CS14 | 2M Sodium Octanoate | NaOH (27% (w/w)) Octanoic Acid | 281 288 | 7.8-8.4 | — |
| CS15 | Acetic Acid | $CH_3COOH$ | 1045 | — | — |
| CS17 | DE-FF2 Equilibration/Wash | $CH_3COOH$ NaOH (27% w/w) | 1.50 1.66 | 4.5-4.7 | 0.85-1.05 |
| CS18 | Positive-mode DE-FF2 Elution | $NaH_2PO_4 \cdot 2H_2O$ NaOH (27% w/w) | 8.58 4.07 | 6.8-7.0 | 5.5-6.5 |
| CS19 | SP-FF2 Equilibration/Wash | $CH_3COOH$ NaOH (27% w/w) | 1.80 3.52 | 5.2-5.4 | 1.8-2.1 |

TABLE 3-continued

Chromatography solutions for the purification of albumin

| Solution | | | Concentration | | Conductivity |
|---|---|---|---|---|---|
| No. | Name | Constituent | $(g \cdot L^{-1})$ | pH | $(mS \cdot cm^{-1})$ |
| CS20 | PBA Equilibration/Wash | Glycine<br>NaCl<br>NaOH (27% w/w)<br>$CaCl_2 \cdot 2H_2O$ | 7.51<br>5.84<br>0.95<br>7.35 | 8.3-8.6 | 18-22 |
| CS21 | 20%(w/w) Acetic Acid | $CH_3COOH$<br>$H_2O$ | 205<br>820 | 1.9-2.2 | 1.8-2.0 |
| CS22 | Final pH Adjustment | $Na_2HPO_4$<br>NaOH (27% w/w) | 71.0<br>37.0 | 11.2-11.4 | 43-49 |
| EXO4 | Final pH adjustment alkali | NaOH (47% w/w)<br>$H_2O$ | 42.6<br>970 | $\geq 12$ | 80-120 |
| EXO5 | Final pH adjustment acid | HCl (37% w/w)<br>$H_2O$ | 19.7<br>982 | $\leq 1.5$ | 60-90 |

All weighings are ±2%, for this particular example.

The centrate from a fermentation is prepared, or conditioned, for chromatography on a cation exchange matrix while protecting the rHA from polymerisation and protease activity. However if the yeast strain is not deficient in the proteases that degrade rHA at the pH required to purify the rHA then the culture supernatant should be pasteurised, for example by a heat treatment of 50-70° C. for 30 minutes to 5 hours, as detailed in WO 94/03636. Typically 1-10 mM sodium octanoate is sufficient to protect the rHA from heat denaturation and 30 seconds up to 10 minutes at temperatures of 60-80° C. adequate to inactivate the proteases in a batch or flowthrough procedure. Pasteurisation may also be desirable if HSA is used.

The conditioned centrate is then loaded onto the column at a flow rate of, for example, 0.07-0.75 bed volumes/min, preferably 0.3-0.6 bed volumes/min, in this example 0.5 bed volumes/min, and then the column is washed with one or more solutions to remove residual contaminants. The column is washed first with, for instance, eight volumes of 10-100 mM, preferably 30-70 mM, for example 50 mM acetate, pH3.9-4.1, 0.6-0.8 mS·cm$^{-1}$ (CS02). The column is then washed with four volumes of a high salt buffer containing 1-3M NaCl, preferably 2M NaCl, in sodium acetate buffer (for example 10-50 mM sodium acetate, preferably about 27 mM, pH3.5-4.5, preferably pH4.0 (CS03) and then ten volumes of CS01. The albumin is eluted with, and collected in an acetate/octanoate buffer (for example 40-120, preferably 60-100, eg 85 mM acetate, and 2-50 mM, preferably, 2-20 mM, eg 5 mM octanoate, as in CS04). The collection of albumin starts when the UV signal rises above 0.6 $A_{254}$/cm, and collection continues until the UV signal Falls below 0.36 $A_{254}$/cm. The column is then cleaned using 0.25-3.0M NaCl and 0.05-2% detergent (CS05) and then 0.1-1.0M NaOH (CS06), then stored in diluted (10-50 mM) NaOH (CS07), In this example, the flow rate for the equilibration, loading and wash steps is 0.5 bed volumes per minute. For elution of the albumin, a flow rate of 0.04-0.6 bed vol/min, preferably 0.15-0.35, in this example 0.25 bed vol/min is used.

Anion Exchange Chromatography

The eluate from the cation exchanger is then diluted to below 10 mS·cm$^{-1}$, preferably less than 5 mS·cm$^{-1}$, especially below 2.5 mS·cm$^{-1}$ and then loaded onto an anion exchange resin such as QMA-Spherosil, DEAE-Spherodex, Q-Hyper D, DEAE-cellulose, QAE-cellulose, or TMAE, DMAE, or DEAE Fractogel. Preferably, the matrix is the commercial anion exchange matrix DEAE Sepharose-FF (Pharmacia), bed flow path length of 11.0±1.0 cm, pre-equilibrated with the cation elution buffer (CS04) and then equilibrated with three column volumes of CS01. The albumin is loaded onto the matrix at 30±10 g monomeric albumin per liter of matrix and then the matrix is washed with dilute tetraborate buffer, for example 15-25 mM potassium tetraborate or sodium tetraborate (CS08), which has the effect of raising the pH to approximately 9.2, and then the albumin is eluted with a more concentrated tetraborate buffer (for example 80-150 mM potassium tetraborate, preferably 110 mM potassium tetraborate (CS09)). The matrix is cleaned with salt/detergent (CS05) and then NaOH(CS06) before storage in dilute NaOH (CS07). The eluate from the anion exchange matrix is then loaded onto an affinity matrix.

Affinity Chromatography

This step further purifies the rHA with respect to a 45 kDa N-terminal albumin fragment, yeast antigens and pigment. The affinity matrix may comprise any Cibacron Blue type of dye which binds albumin, for example Reactive Blue 2, Procion Blue HB, Blue Sepharose, Blue Trisacryl and other anthraquinone-type compounds. Preferably, the matrix is the "Delta Blue"[7] Matrix (DBA), prepared as described in WO 96/37515.

The method uses DBA at a bed flow path length of 11.0±1.0 cm. The DBA is equilibrated in ammonium acetate buffer (100-300 mM, preferably 200-275 mM, for example 250 mM as in CS10) and the albumin applied at 7.0-14.0 g/L, preferably 8.0-12.0 g/L, in this example 10.0±1.0 g/L. Equilibration, load and wash steps are performed at flow rates of 0.05-0.30 bed vol/min, preferably 0.15-0.27, in this example 0.25 bed vol/min. All other steps are performed at 0.20 bed vol/min. When loading is complete, the column is washed to remove contaminants with 1-5 volumes of ammonium acetate buffer 10-30 mS cm$^{-1}$, preferably 15-25 mS cm$^{-1}$, for example CS10, preferably 5 column volumes. The albumin is eluted with a strong salt and phosphate solution (1.0-3.0M NaCl, for example 1.5-2.5M NaCl or 2.0M NaCl, and 5-100 mM, eg 50 mM phosphate, as in CS11. The column is then cleaned using CS06 and stored in CS07.

The eluate from the DBA column is then concentrated and diafiltered in preparation for purification using phenyl boronate agarose (PBA) chromatography. DBA ultrafiltration can be performed with any ultrafiltration membrane used in protein concentration with a nominal molecular weight cut off of 30,000 or less, preferably a polyethersulphone type membrane (eg Filtron Omega series) of 10,000 nominal molecular weight cut off. DBA eluate is concentrated and then diafiltered at ≈100 g rHA·L$^{-1}$ against at least 5 volumes of water followed by at least 5 volumes of CS20. At the end of diafiltration, the retentate may be further concentrated if required and the equipment washed out with CS20 to increase step recovery. The concentration of the final retentate should be in the range 20-120 g rHA·L$^{-1}$, preferably 70-120 g·L$^{-1}$, or as in this example 100±10 g rHA·L$^{-1}$. After use, the membranes are treated by flushing out residual protein with water, cleaning with CS06 and storage in CS07.

PBA is an affinity step to remove glycoconjugates, such as glycoproteins, glycolipids and poly-, oligo- and monosaccharides, and utilises immobilised aminophenylboronic acid as the ligand. The aminophenylboronic acid is covalently coupled via a spacer to an insoluble matrix such as polyacrylamide, agarose, cellulosic or organic polymers. U.S. Pat. No. 4,562,251 (incorporated herein by reference) describes suitable methods for making diborotriazine or monoborotriazine agarose: (1) triazine is O-linked to agarose first and then linked with 3-aminophenylboronic acid (APBA) in a second reaction. (2) Triazine is reacted with APBA first to produce either mono or diborotriazine. These are then O-linked via the free chlorine on the triazine to the —ONa activated agarose to produce either mono or disubstituted agarose.

An earlier patent, U.S. Pat. No. 4,269,605, contemplates a variety of activation methods, including epichlorohydrin activation of agarose, preferred herein. Commercially available matrices include Amicon's PBA30 and Sigma's acrylic beaded aminophenylboronate.

It has been found to be particularly beneficial to use a buffer containing glycine (10-500 mM, for example 25-200 mM, preferably 50-150 mM, in this example 100 mM), NaCl (0-500 mM, for example 25-200 mM, preferably 50-150 mM, in this example 100 mM) and CaCl$_2$ (5-250 mM, preferably 10-100 mM, in this example 50 mM), pH8.0-9.5, preferably, pH 8.0-9.0, in this example pH8.5 (CS20).

The PBA column uses a flow path length of 11.0±1.0 cm and is pre-equilibrated with the buffer as described above, eg CS20. The column is loaded at less than 1 column volume, preferably less than 0.5 column volumes, in this example $\leq$0.35 column volumes. The PBA is ran as a negative step and therefore the albumin is collected in the flow through and wash from the column. All chromatographic steps can be performed at flow rates of 0.005-0.3 bed vol./min.

Preferably the equilibration and cleaning of the column are carried out at a higher flow rate, eg 0.19 bed vol./min, than the load and collection of the albumin solution, which is preferably carried out at a flow rate of 0.01-0.05, preferably 0.025 bed vol./min. The column is then cleaned with salt (CS03), borate buffer (CS09), NaOH(CS06) and then stored in dilute NaOH(CS07).

Following PBA chromatography the albumin solution is concentrated and diafiltered to prepare for a negative mode cation exchange step. The combination of this diafiltration step and the negative mode cation exchange chromatography substantially reduces the relative concentration of nickel ions.

PBA ultrafiltration can be performed with any ultrafiltration membrane used in protein concentration with a nominal molecular weight cut off of 30,000 or less, preferably a polyethersulphone type membrane (eg Filtron Omega series) of 10,000 nominal molecular weight cut off. The collected PBA Flow Through is adjusted to pH5.3±0.5 with CS21, concentrated and then diafiltered at $\approx$100 g rHA·L$^{-1}$ against at least 7 volumes of CS19. At the end of diafiltration, the equipment is washed out with CS19 and further CS19 added as required to give a retentate concentration of 50±10 g rHA·L$^{-1}$. Finally, sodium octanoate is added to give a final concentration of approximately 2-15 preferably 5-10, more preferably 6-9, and in this example 6 mM, eg CS14 is added to 3 mL·L$^{-1}$.

After use, the membranes are treated by flushing out residual protein with water, cleaning with CS06 and storage in CS07.

The albumin solution is then subjected to a second cation exchange step using, for instance, SP-FF Sepharose (Pharmacia), this time in the negative mode, ie the albumin passes through the matrix, rather than being retained. The conditions are such that mannosylated albumin binds to the matrix. The buffer is preferably a sodium acetate buffer (5-110 mM acetate, preferably 10-50 mM, in this example 30 mM), pH 5.2-5.4, CS19). Other buffers which can buffer in the appropriate range may be used, such as a citrate phosphate buffer. Suitably, the buffer has a conductivity of about 2 mS·cm$^{-1}$. The column has a flow path length of 11.0±1.0 cm, with the albumin loaded to 10-250 g·L$^{-1}$ preferably 20-70 g·L$^{-1}$ and in this example 50±15 g or 50±10 g·L$^{-1}$ matrix. Since this is a negative step, the albumin is collected in the flow through and wash.

Following this cation exchange step, the albumin is subject to negative mode anion exchange chromatography. This step removes yeast antigens as measured by ELISA and Western blot. The collected flow through and wash from the second cation exchange step is adjusted to pH4.60±0.10 with CS21, diluted to 1.05±0.1 mS·cm$^{-1}$ with water and the rHA purified using the following conditions. The step uses an anion exchange matrix such as DE-FF Sepharose (Pharmacia) at a flow path length of 11.0±1.0 cm and the albumin is loaded to 50-250 g·L$^{-1}$, preferably 150±50 g·L$^{-1}$, matrix. Since this is a negative step, the albumin is collected in the flow through and wash. The pH of the Flow Through and Wash is then adjusted to 7.0±0.1 with CS22.

Alternatively, as described in Example 9, pH-adjustment may occur in the Final UF feed vessel instead of being performed on the DEAE flow through and wash.

While Example 1 has been illustrated with reference to a pmt1 mutant, it should be appreciated that the purification process of the present invention is equally applicable to host cells which are not mutant at this locus, or indeed which are not mutant at any other pmt locus

EXAMPLE 2

Two assays were used to investigate centrate quality. The poorer the centrate quality the worse the "robustness" of the yeast cells.

The two assays were:
1. Determination of the absorbance of centrate at 600 nm ($A_{600}$).
2. Determination of the wet weight of particles in the centrate (WW).

In both the assays, the higher the value the poorer the centrate quality.

The centrate quality of three different yeast strains tender two different pH conditions grown in fed-batch fermentation were compared.

TABLE 4

A600 and WW values for three different rHA producing strains in fed-batch fermentation grown at two different pH values.

| Specific gene deletions | $A_{600}$ | WW (g · L$^{-1}$ centrate) |
|---|---|---|
| | Grown at pH 5.5 | |
| pmt1-/hsp150-/yap3- | 1.39 (0.52, 24) | 12.4 (4.9, 23) |
| hsp150-/yap3- | 1.11 (0.62, 9) | 9.1 (2.9, 7) |
| yap3- | 0.58 (0.34, 10) | 3.9 (2.0, 10) |

TABLE 4-continued

A600 and WW values for three different rHA producing strains
in fed-batch fermentation grown at two different pH values.

| Specific gene deletions | $A_{600}$ | WW (g·L$^{-1}$ centrate) |
|---|---|---|
| | Grown at pH 6.4 or 6.5 | |
| pmt1-/hsp150-/yap3- | 0.41 (0.17, 6) | 2.6 (0.8, 6) |
| hsp150-/yap3- | 0.47 (0.19, 8) | 4.6 (1.4, 7) |
| yap3- | 0.41 (0.08, 6) | 2.1 (0.8, 6) |

In the first column the specific gene deletions are indicated. Values in parentheses are standard deviation and number of samples.

From the Table above it can be concluded that at pH 5.5, the multiply-gene deleted strains yield an inferior centrate, whereas at pH6.4 or 6.5, the deleterious effect of these further gene deletions is avoided.

EXAMPLE 3

This example was performed in the same manner described in Example 1, but utilised a strain which is not pmt1 mutant. This strain was also grown at two different pH control values, and the wet weight content of the centrate determined as described in Example 1. The benefit of growth at the elevated pH control point is also seen for this strain of yeast; demonstrated in Table 5, where a significant reduction in the wet weight content of a culture supernatant is shown when the yeast is cultured in the pH range 6.3 to 6.5 compared to pH5.5.

TABLE 5

Relationship between centrate quality and fermentation pH for non-pmt1 strain.

| Fermentation pH | Wet Weight Content of Supernatant (g·L$^{-1}$) |
|---|---|
| 5.5 | 10.0 (2.3, 4) |
| 6.3-6.5 | 4.6 (1.4, 7) |

Values in parentheses are standard deviation and number of samples.

Thus, rather than control the pH at approximately 55, it is beneficial to have a control set point between pH6.20 and pH6.70, preferably between pH6.3 and 6.5. At such a higher pH, the quality of the centrate is significantly improved due to reduced cell lysis

EXAMPLE 4

This Example was performed in a similar manner as described in Example 1, with the following differences. The yeast *Pichia pastoris*, strain GS115 (Invitrogen) was grown using the same conditions and medium as described above, but using a pH1 controller set at 5.90; controlled at 5.90+0.20, a specific growth rate of 0.10 h$^{-1}$ with glucose as a carbon source. The batch phase duration was 28 h, and the feed phase duration was 42 h. Recombinant human albumin was added once the feed phase had commenced, providing a final concentration of 3.8 g rHA·L$^{-1}$ culture at the end of the fermentation. The rHA used to spike the *Pichia* culture had been purified but not in accordance with the purification process of the invention.

The rHA from the *Pichia* fed-batch culture medium was then purified in accordance with the purification process described in Example 1.

EXAMPLE 5

This Example describes the analysis of rHA purified from *Pichia* culture media as described in Example 4.
Immunoassay Data Immunoassays were performed on: (i) the rHA purified from the *Pichia* culture media; (ii) the rHA used to spike the culture media; and (iii) on albumin produced by *Saccharomyces cerevisiae* which had purified in accordance with the present invention.
Western Blot Summary

| Antibody Batch Number | Ig9601 |
|---|---|
| Gel Type | 4-12% SDSNR NOVEX GELS |
| Milk Type | UHT |
| Exposure Time | 20 seconds |

Ig9601 was raised against a non-albumin producing *Saccharomyces cerevisiae* strain and thus can be used to detect yeast antigens.

The western blot showed that the yeast antigen profile of the albumin derived from the *Pichia* culture medium contained fewer and less intense bands than the material used to spike the *Pichia* fermentation. The *Pichia*-derived albumin yeast antigen profile was very similar to the *Saccharomyces*-derived profile.
ELISA Blot Summary Yeast antigen impurities in the albumin purified from the *Pichia* culture medium and for the albumini used to spike the *Pichia* medium were quantified by ELISA using Ig9601.

The yeast antigen content of the albumin purified from the *Pichia* culture medium was below the detectable limit of the assay (approximately 0.004 µg.g$^{-1}$), and the antigen content for the albumin used to spike the *Pichia* medium was 0.62 µg.g$^{-1}$.
Con A Binding Material The Con A assay described in Example 9 was performed on albumin purified from the *Pichia* culture medium and for the albumin used to spike the *Pichia* medium. The content of Con A binding material for the former was 0.22% (w/w) and for the latter it was 0.57% (w/w).

The level of Con A binding material in the albumin purified from the *Pichia* culture medium is similar to that of albumin purified from *Saccharomyces cerevisiae* in accordance with the invention (see Table 6), when the latter is not produced from a pmt1 mutant.

The purity analyses confirm that the process of the invention can be successfully used to purify albumin from yeast other than *Saccharomyces cerevisiae* (eg *Pichia*) and that albumin of similar purity to that purified from *Saccharomyces cerevisiae* can be obtained.

EXAMPLE 6

In Example 1a negative mode anion exchange chromatography step (DE-FF2) followed the second cation exchange chromatography step (SP-FF2). In an alternative purification process the second cation exchange chromatography step may be followed by a positive mode anion exchange chromatography step.

From the SP-FF2 eluate at pH5.3 approx. the pH needs to be increased to pH7. There are two means detailed below, pH adjustment and diafiltration. The latter appeared to give a better quality product.

DE-FF2 (A)

SP-FF2 flow through and washings were pH adjusted to pH 7.0 with 0.5 M disodium hydrogen orthophosphate. This material was loaded onto a DEAE under standard positive conditions to give a matrix loading of 40 g rHA·L$^{-1}$ matrix, the pH and conductivity of the load were 7.0 and 1.29 mS·cm$^{-1}$ respectively.

DE-FF2(B)

SP-FF2 flow through and washings were diafiltered vs. 10 vol. 10 mM sodium phosphate pH 7.0, concentrated and diluted with buffer to 50 g·L$^{-1}$ and loaded onto a DEAL under standard positive conditions. The pH and conductivity of the load was 7.0 and 1.43 mS·cm$^{-1}$ respectively.

The albumin from DE-FF2A/DE-FF2B is suitably eluted by a 45-55 mM sodium phosphate buffer (pH7.0).

EXAMPLE 7

Figure 9:
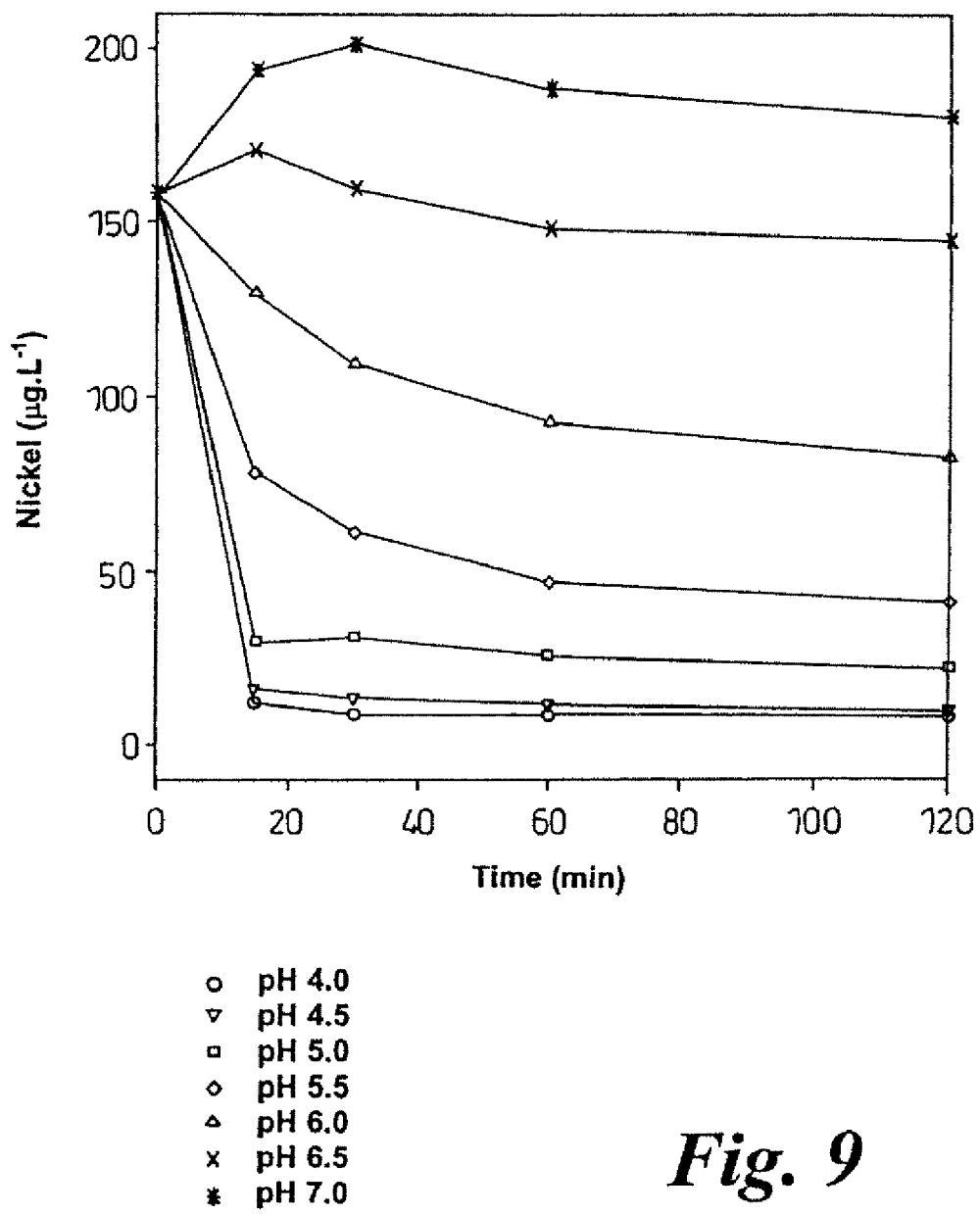
FIG. 9 shows the effect of pH and time on nickel removal from rHA by Chelex™.

The kinetics of nickel removal from rHA by treatment with low pH were investigated (see FIG. 9). The results showed that between pH 4 and 4.5 both the rate and extent of nickel removal were independent of pH, but that at pH 5 the rate of removal slowed slightly. Both the rate and extent of nickel removal decreased with increasing pH across the range 5-6.5 with little or no removal above pH 6.5.

EXAMPLE 8

Purification of human serum albumin from a sample of cryo-poor plasma paste (Centeon Pharma GmbH) was achieved using the purification process detailed in Example 1.

Recoveries of HSA at each chromatography step were predominantly comparable to the anticipated rHA recovery at the same stage, with the exception of the PBA column. Here, the recoveries were much lower than expected which may have been due to removal of glycated albumin.

EXAMPLE 9

This Example illustrates the concentration, diafiltration and formulation of the highly purified rHA into a suitable product, in this instance 20% (w/v) albumin. This procedure is carried out in two stages, namely final ultrafiltration (UF) and Formulation.

Final UF reduces nickel concentration by diafiltration at low pH and presents rHA in a defined aqueous environment, using water of an appropriate grade, Final UF begins with transfer of DEAE flow through and wash to the Final UF feed vessel. As described below, the albumin is then concentrated, diafiltered pH adjusted to pH7.0 and further concentrated.

If DLE-FF2 is run in positive mode, the DE-FF2 eluate may be used instead of, or in addition to, the DEAL flow through and wash.

Following transfer of the DE-FF2 flow through and wash (or eluate if DE-FF2 is run in positive mode), the rHA-containing process stream is sequentially subjected to primary concentration, diafiltration and secondary concentration phases in an ultrafiltration system fitted with cellulosic membranes with a nominal molecular weight cut off limit of 10,000. The initial concentration step increases the rHA concentration to approximately 100 g·L$^{-1}$ and is immediately followed by the continuous diafiltration phase where the rHA is diafiltered against at least 5, preferably at least 7 retentate volume equivalents of water-for-injection, preferably a 50 mM salt solution to remove ammonia. Following diafiltration the pH is adjusted to 7.0 and, the secondary concentration phase further increases the rHA concentration to 275-325 g·L$^{-1}$. At the end of UF the retentate is transferred to the bulk product formulation vessel.

Instead of pH-adjustment being performed on the DEAE flow through and wash, pH adjustment may occur in the Final UF feed vessel, preferably between the diafiltration process and the secondary concentration phase. Preferably, the diafiltration retentate is adjusted to pH 7±0.1 with EX04. If the pH exceeds 7.1 but remains <pH8.5 then the pH can be decreased with EX05.

The formulation step produces rHA in an appropriate chemical environment and at an appropriate concentration suitable for bulk: product sterile filtration and filling. The transferred Final UF retentate is analysed to determine concentrations of albumin, sodium and octanoate. These quantities are taken into account and any necessary further amounts of stock sodium chloride and sodium octanoate excipient solutions and appropriate grade water added to achieve the bulk formulation specification. The final albumin concentration may be 150-250 g·L$^{-1}$ or 235-265 g·L$^{-1}$ with a sodium concentration of 130-160 mM. Any other feasible albumin concentration may be made, however, with, for example, a minimum concentration of at least 4% (w/v), preferably 4-25% (w/v). Formulation is complete following addition of appropriate conventional pharmaceutically acceptable excipients, such as polysorbate 80 or those specified in the US Pharmacopoeia for human albumin, and diluting water.

A final concentration of 0.08 mmoles sodium octanoate per gram of albumin may be desirable. The product is sterile and non-pyrogenic. There may be up to 1% dimeric albumin but no larger polymers or aggregates are detectable.

EXAMPLE 10

This Example illustrates the analysis that is carried out to establish the purity of albumin purified in accordance with the present invention. Unless stated otherwise, all of the assays are performed on albumin which has been purified according to Example 1 and formulated according to Example 9.

Glycation of rHA

A microassay for glycated protein has shown that rHA purified in accordance with the invention is not substantially modified by non-enzymic glycosylation (glycation). The microassay measures the stable Amadori product (AP) form of glycated protein, by oxidation of the C-1 hydroxyl groups of AP with periodate. The formaldehyde released by periodate oxidation is quantitated by conversion to a chromophore, diacetyldihydrolutidine (DDL), by reaction with acetylacetone in ammonia. DDL is then detected calorimetrically. The samples were assayed after desalting using a Pharmacia PD-10 (G25 Sephadex) column and then the albumin in the samples was re-quantitated by the Bradford method and 10 mg albumin was assayed. A fructose positive control was included, and the absorbances were read on a Shimadzu UV 2101 spectrophotometer at is 412 nm. For every mole of hexose one mole of Amadori product is formed.

| Sample | Moles Amadori Product/Moles Albumin |
| --- | --- |
| A | 0.79 |
| B | 0.76 |
| C | 0.41 |
| D | 0.48 |
| E | 0.46 |
| F | 0.22 |

-continued

| Sample | Moles Amadori Product/Moles Albumin |
|---|---|
| G | 0.41 |
| H | 0.37 |
| I | 0.54 |
| J | 0.76 |
| K | 0.84 |
| L | 0.50 |
| M | 0.43 |
| N | 0.59 |
| O | 0.41 |
| P | 0.18 |
| Q | 0.24 |
| R | 0.04 |

Samples A-Q are commercially available HSA products from US, Europe and Japan (mean=0.49±0.20). Sample R is rHA purified according to the invention.

Analysis of C-terminus

An important aspect of the quality control of recombinant proteins is the conformation and stability of the pre-determined primary structure. Analysis of the C-terminal tryptic peptide in commercially available USA and rHA purified according to the invention by N-terminal sequencing and FAB mass spectometry indicated the presence of a truncated peptide, lacking the C-terminal leucine in HSA. The Des-Leu C-terminal tryptic peptide was detected in commercial HSA at approximately 5-10% (not quantitative), but could not be detected in the rHA of the invention, even after 6 months at 30° C. The Des-Leu peptide could not be detected in the USA 12 weeks at 30° C., and the peak for the full length C-terminal peptide was very diminished compared to the other samples, indicating that perhaps this had undergone further C-terminal degradation.

These results indicate that the rHA, purified in accordance with the invention, has a stable and full length carboxy-terminus, whereas USA previously available from commercial sources appears to be heterogeneous by comparison.

Nickel Ion Content of rHA Prepared According to the Invention

Measuring Instrument:

SIMAA 6000, Perkin Elmer Furnace: CTT (Constant Temperature Tube) using detection at 232 nm, 2470° C.

Calibration:

The method is based on a three-point calibration (18/30/60 lg/L standard solutions from Perkin Elmer). After the calibration, a blank of purified water is measured. The control standard is measured after the blank and at the end of each test series (Ni-Standard 20 lg/L, certified standard from Perkin Elmer).

Sample Preparation:

Each assay is the result of a determination in duplicate which also valid for the calibration and the control standard. Depending on the expected Ni concentration, the sample is diluted in an appropriate ratio to work with a Ni-concentration that is within the calibration range. Samples with a protein concentration of 10% or more have to be diluted at least 1:5 in any case. Dilution is with purified water.

Rinsing solution for the sample capillary: 2 L purified water mixed with 0.5 mL Triton X100. Each test series includes a system suitability test.

Requirements:

1. Correlation coefficient of the calibration at least 0.99000. If not, the calibration has to be repeated one time. If the calibration does not comply with the requirement a second time, an error analysis has to be carried out.

2. Characteristic mass measured with the 30 lg/L-Standard may not exceed the theoretical value of 20 pg/0.0044A-s by more than 20 percent.

Characteristic Mass $m_0$:

That amount of the analyte in picogram (pg) that contributes an absorption of 1 percent. An absorption of 1 percent corresponds to 0.0044 A-s (ampere seconds).

$$m_0 = \frac{\text{volume Standard (mL)} * \text{concentration (mg/L)} * 0.0044 A - s}{\text{absorption sample} * \text{absorption blank}}$$

3. The measured concentration of the control standard has to be within the confidence range (2 s/3 s criterion).

Calculation:

The measuring instrument calculates the result according to the following term:

$$\text{Result } (\mu g\, Ni/L) = \left(\frac{A1}{\text{slope}} \pm \frac{A2}{\text{slope}}\right) : 2 * V$$

A: absorption
slope: slope of the calibration curve (linear regression)
V: dilution A modifier is not used.

| Sample | [Nickel]/[rHA] (µg/g) | |
|---|---|---|
| | Batch 1 | Batch 2 |
| PBA load | 0.73 | 0.74 |
| PBA flow through and wash | 0.41 | 0.43 |
| SP-FF2 load | 0.06 | 0.06 |
| SP-FF2 flow through and wash | <0.03 | <0.03 |
| DE-FF2 flow through and wash | 0.14 | 0.28 |

Analysis of Medium and Long Chain Fatty Acids

The fatty acids profiles of albumin according to the invention and commercially available TISA were analysed by acidic solvent extraction and gas chromatography of the free fatty acids using a C17:0 internal standard. No abnormal fatty acids have been detected in the albumin of the invention by this method although the profiles for the rHA and HSA showed significant differences. As expected, both showed large amounts of the added stabiliser, octanoate (C8:0). Apart from this, commercial HSA was characterised by predominantly C16:0, C16:1, C18:0, C18:1 and C18:2 whilst the albumin of the invention contained mainly C10:0 and C12:0 and occasionally C14:0. Further experiments showed that the levels of C10:0 and C12:0 in rHA final product correlated with the levels of these contaminants in the octanoate used for the latter stages of the purification process.

Preferably, the total level of C18 fatty acids does not exceed 1.0% (mole/mole) of the level of octanoate, and preferably does not exceed 0.5% of that level. Moreover, in the albumin of the invention, the level of C18:2, C18:3 and C20 fatty acids is generally undetectable. In commercial HSA, there may typically be about 0.4 mmoles C18 fatty acids per mole of albumin. In the product of the invention, there are typically no detectable C20 fatty acids and only about 0.02 moles C18 fatty acids per mole of albumin.

SDS Reducing Polyacrylamide Gel Electrophoresis

This assay was performed as described in WO 96/37515. The assay showed that rHA of the invention consists of a single polypeptide chain which when treated with a reducing agent (β-mercaptoethanol) migrates as a single band (monomer) on SDS reducing polyacrylamide electrophoresis (PAGE) which indicated that the proportion of albumin present as a monomer is at least 99.9%.

Gel Permeation High Pressure Liquid Chromatography

25 ☒ of a 10 mg/ml solution of albumin purified in accordance with the invention which had been formulated to 25% w/v was injected onto a TSK3000SWXL column on a Shimiadzu LC6A HPLC and found to contain less than 0.1% polymeric albumin. This result indicates that the formulation as described herein has no detrimental effect on the polymer/aggregate content of the purified albumin.

Two Dimensional Gel Electrophoresis

2 μg rHA of albumin prepared by the process of the invention was subject to two-dimensional electrophoresis using a Millipore Investigator system. The separation in the first dimension was a pH 3-10 isoelectric focusing gel and was followed by a 10% polyacrylamide/SDS gel in the second dimension. On staining of the gel with Coomassie Blue, only one spot was visible, indicating the presence of only one protein species.

Mannosylated Albumin/Con A Assay

Concanavalin A (Con A) binds molecules which contain α-D-mannopyranosyl, α-D-glucopyranosyl and sterically related residues. In the Con A assay, Con A Sepharose (Pharmacia, Cat. No, 17-0440-01) affinity chromatography of recombinant Human Albumin (rHLA) and/or Human Serum Albumin (HSA) is used to determine the content of mannosylated albumin.

Recombinant human albumin (rHA) is diluted to 5% (w/v) rHA with 145 mM sodium chloride then 1:1 with Con A dilution buffer (200 mM sodium acetate, 85 mM sodium chloride, 2 mM magnesium chloride, 2 mM manganese chloride, 2 mM calcium chloride pH5.5). 100 mg rHA is then loaded onto an equilibrated 2 mL Con A Sepharose column which is then washed (5×4 mL) with Con A equilibration buffer (100 mM sodium acetate, 100 mM sodium chloride, 1 mM magnesium chloride, 1 mM manganese chloride, 11 mM calcium chloride pH5.5). The column is eluted with 6 mL Con A elution buffer (100 mM sodium acetate, 100 mM sodium chloride, 0.5M methlyl-α-D-mannopyranoside pH5.5).

Monomeric albumin in the Con A load (diluted to about 0.1 mg·mL$^{-1}$) and eluate (assayed neat) are quantified by GP.HPLC using a 0-0.2 mg·mL$^{-1}$ rHA standard curve and the Con A binding albumin monomer recovered in the eluate is expressed as a percentage of the load.

Figure 8:
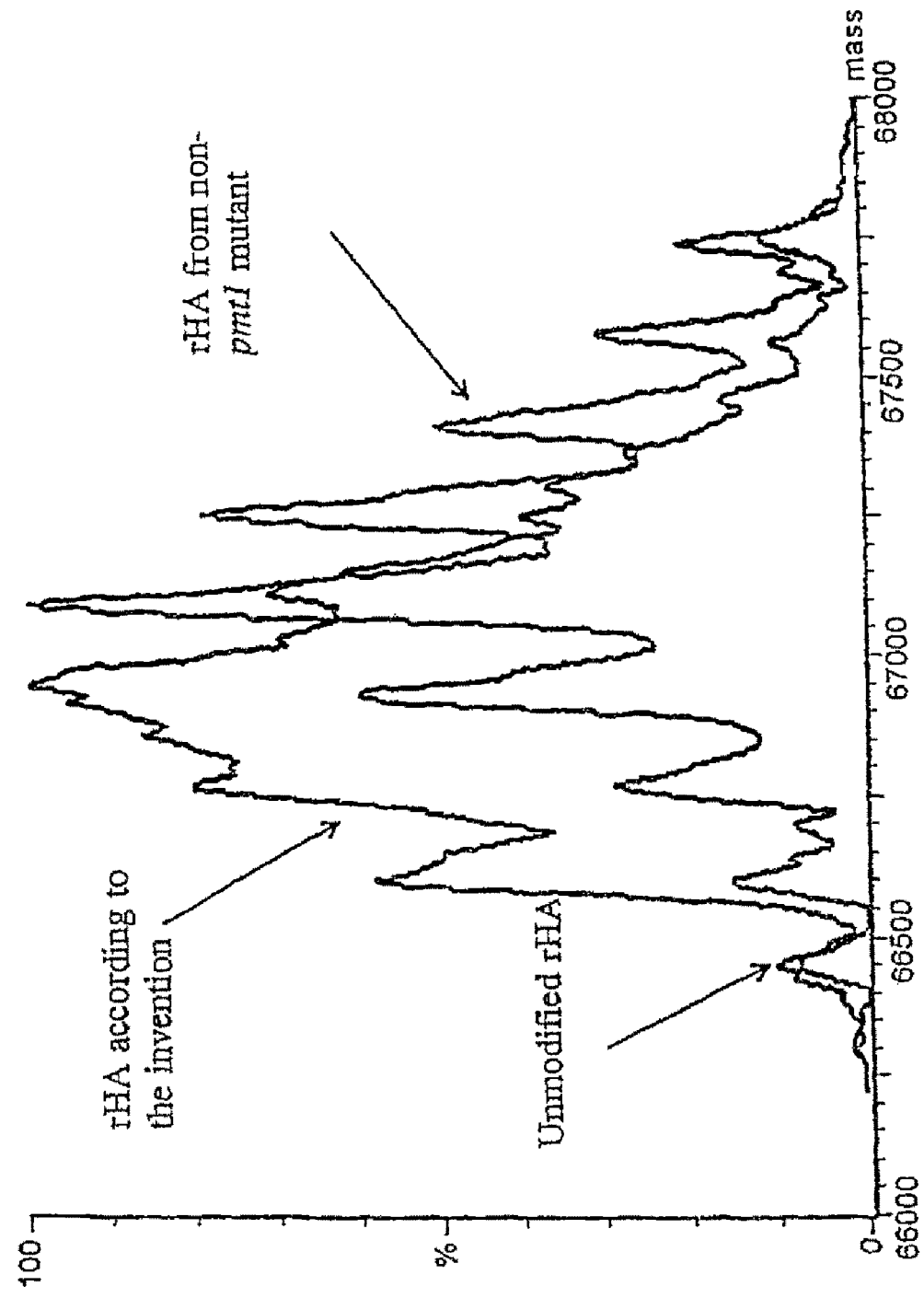
FIG. 8 shows electrospray mass spectrometry of conA-binding rHA fraction from rHA prepared according to the invention.

ConA-binding rHA was further analysed by electrospray mass spectrometry (FIG. 8). This indicated that, in addition to a reduction in the amount of conA-binding rHA, the extent of modification of the conA-binding rHA was reduced.

Analysis of Colour

The absorbance of a 5% (w/v) solution of the final product in a 1 cm cuvette was measured at 350 nm, 403 nm and 500 nm and calculated in terms of absorbances per gram of albumin/liter per cm pathlength (ie ABS·L·g$^{-1}$·cm$^{-1}$). The albumin of the invention has the following values:

| Wavelength (nm) | Mean absorbance (n = 4 batches) (L · g$^{-1}$ · cm$^{-1}$) |
| --- | --- |
| 350 | 5.75 × 10$^{-3}$ |
| 403 | 1.7 × 10$^{-3}$ |
| 500 | 0.4 × 10$^{-3}$ |

Generally, the albumin of the invention does not exceed respective absorbiances of 8.0×10$^{-3}$, 3.0×10$^{-3}$ and 0.75×10$^{-3}$ at the said three wavelengths.

Assays of a number of commercially available HSA preparations revealed higher absorbances at these wavelengths (see Table 7).

TABLE 7

Absorbance (L · g$^{-1}$ · cm$^{-1}$) of prior art HSA preparations

| SAMPLE | A$_{350}$ | A$_{403}$ | A$_{500}$ |
| --- | --- | --- | --- |
| 1 | 9.95 × 10$^{-3}$ | 4.10 × 10$^{-3}$ | 0.8 × 10$^{-3}$ |
| 2 | 9.25 × 10$^{-3}$ | 5.36 × 10$^{-3}$ | 1.1 × 10$^{-3}$ |
| 3 | 7.40 × 10$^{-3}$ | 3.26 × 10$^{-3}$ | 0.6 × 10$^{-3}$ |
| 4 | 7.20 × 10$^{-3}$ | 3.60 × 10$^{-3}$ | 0.6 × 10$^{-3}$ |
| 5 | 8.68 × 10$^{-3}$ | 4.08 × 10$^{-3}$ | 0.8 × 10$^{-3}$ |
| 6 | 11.45 × 10$^{-3}$ | 6.26 × 10$^{-3}$ | 1.2 × 10$^{-3}$ |
| 7 | 7.20 × 10$^{-3}$ | 3.70 × 10$^{-3}$ | 0.8 × 10$^{-3}$ |
| 8 | 6.82 × 10$^{-3}$ | 4.78 × 10$^{-3}$ | 1.8 × 10$^{-3}$ |

Endotoxin

A solution of drug product is assayed using Limulus amoebocyte lysate by kinetic turbidimetric measurement at 340 nm, at a temperature of 36.5-37.5° C. using a automatic endotoxin detection system (eg, LAL 5000E). A standard curve is constructed from known concentrations of a standard endotoxin preparation, negative controls and test material solution spiked with a known quantity of standard endotoxin are also included in the assay. The change in turbidity of the reaction mixture is measured over time and a log-log regres-

TABLE 6

Clearance of conA-binding rHA through the process. Batches 1-4 are derived from a pmt1 mutant, whereas batch 5 is derived from a non-mutant strain.
ConA-binding rHA (% of load)

| Batch 1 | | Batch 2 | | Batch 3 | | Batch 4 | | Batch 5 | |
| --- | --- | --- | --- | --- | --- | --- | --- | --- | --- |
| PBA FT&W | 0.14 | PBA FT&W | 0.16 | PBA FT&W | 0.15 | PBA FT&W | 0.13 | PBA FT&W | 0.55 |
| SP-FF2 FT&W | 0.10 | SP-FF2 FT&W | 0.12 | SP-FF2 FT&W | 0.14 | SP-FF2 FT&W | 0.09 | SP-FF2 FT&W | 0.32 |
| Final Product | 0.10 | Final Product | 0.11 | Final Product | 0.12 | Final Product | 0.07 | Final Product | 0.28 |

(FT&W = Flow Through & Washings)

sion. Any endotoxin in the drug product is quantified against the standard curve and recovery of the endotoxin spike is confirmed. No endotoxin was detected.

Free Thiol

Ellman's Reagent, 5,5'-Dithiobis-(2-Nitrobenzoate) (DTNB) is a specific means of detecting free sulfydryl groups such as cys-SH (Cys-residue 34 in the case of rHA). Idle reaction releases the 5 thio-2-nitrobenzoate ion $TNB^{2-}$ which has an absorption maximum at 412 nm. By measuring the increase in absorbance at 412 nm and dividing by the molar extinction coefficient of the $TNB^{2-}$ ion at 412 nm, the free sulfydryl content of rHA can be calculated.

| Sample | mol · mol$^{-1}$ |
|---|---|
| A | 0.82 |
| B | 0.77 |
| C | 0.77 |
| D | 0.85 |
| E | 0.90 |

The invention claimed is:

1. A process for purifying a recombinant albumin solution, the process comprising—
   (a) subjecting a first recombinant albumin solution of pH 8.0-9.5 buffered with a buffer comprising a divalent cation at a concentration of 5-250 mM, and having a conductivity in the range of 1 to 75 mS·cm$^{-1}$, to an affinity chromatography step which is run in negative mode with respect to the albumin and which utilises an affinity matrix comprising immobilised dihydroxyboryl groups, thereby obtaining a purified albumin solution; and
   (b) subjecting the thus purified albumin solution from step (a) to a concentration step, a diafiltration step and a cation exchange chromatography step, wherein the diafiltration step is conducted at a pH of 2.5-6.0, wherein the cation exchange step is run in negative mode with respect to albumin and under conditions such that glycosylated albumin binds to the cation exchange material, and wherein the albumin solution which undergoes cation exchange chromatography has an albumin concentration of 10-250 g·L$^{-1}$;
   (c) thereby to produce a final recombinant albumin solution having a nickel ion content of less than 100 ng per gram of albumin.

2. The process of claim 1 wherein the diafiltration step is conducted at a pH of 4.0-6.0.

3. The process of claim 1 wherein the diafiltration step is conducted at a pH 5.3±0.5.

4. The process of claim 1 wherein the recombinant albumin solution is obtained from a fungal culture medium obtained by culturing a fungus transformed with an albumin-encoding nucleotide sequence in a fermentation medium, whereby said fungus expresses albumin and secretes it into the medium.

5. The process of claim 1 wherein the cation exchange step utilises a matrix which comprises immobilised sulfopropyl substituents as cation exchangers.

6. The process of claim 1 wherein the albumin solution which undergoes cation exchange chromatography has a pH of 4.5-6.0.

7. The process of claim 1 wherein the albumin solution which undergoes cation exchange chromatography has a pH of 5.0-5.6.

8. The process of claim 1 wherein the albumin solution which undergoes cation exchange chromatography has a pH of 5.2-5.4.

9. The process of claim 1 wherein the albumin solution which undergoes cation exchange chromatography has an albumin concentration of 20-70 g·L$^{-1}$.

10. The process of claim 1 wherein the albumin solution which undergoes cation exchange chromatography has an albumin concentration of 50±10 g·L$^{-1}$.

11. The process of claim 1 wherein the albumin solution which undergoes cation exchange chromatography run in the negative mode with respect to albumin comprises octanoate and/or another fatty acid.

12. The process of claim 11 wherein the albumin solution which undergoes cation exchange chromatography run in the negative mode with respect to albumin has an octanoate ion concentration of 2-15 mM.

13. The process of claim 12 wherein the octanoate ion concentration is 5-10 mM.

14. The process of claim 13 wherein the octanoate ion concentration is 6-9 mM.

15. The process of claim 1 wherein prior to the cation exchange step the albumin solution undergoes (i) pH-adjustment; and/or (ii) conditioning by addition of octanoate and/or other fatty acid.

16. The process of claim 1 wherein the pH of the first albumin solution treated in step (a) of claim 1 is pH 8.0-9.0.

17. The process of claim 1 wherein the pH of the first albumin solution treated in step (a) of claim 1 is pH 8.3-pH8.6.

18. The process of claim 1 wherein the first albumin solution treated in step (a) of claim 1 is buffered with a buffer which comprises divalent cation at a concentration of 10-100 mM.

19. The process of claim 1 wherein the divalent cation in the buffer of the first albumin solution treated in step (a) of claim 1 is calcium.

20. The process of claim 19 wherein the calcium is in the form of CaCl$_2$.

21. The process of claim 1 wherein the first albumin solution treated in of claim 1 is buffered with a buffer which comprises glycine at a concentration of 10-500 mM,; NaCl at a concentration of 0-500 mM; and CaCl$_2$ at a concentration of 5-250mM.

22. The process of claim 21 wherein the buffer comprises glycine at a concentration of 25-200 mM.

23. The process of claim 21 wherein the buffer comprises glycine at a concentration of 50-150 mM.

24. The process of claim 21 wherein the buffer comprises NaCl at a concentration of 25-200 mM.

25. The process of claim 21 wherein the buffer comprises NaCl at a concentration of 50-150 mM.

26. The process of claim 21 wherein the buffer comprises CaCl$_2$ at a concentration of 10-100 mM.

27. The process of claim 1 wherein the first albumin solution treated in step (a) of claim 1 is buffered with a buffer which comprises about 100 mM glycine, about 100 mM NaCl and about 50 mM CaCl$_2$.

28. The process of claim 1 wherein the first albumin solution treated in step (a) of claim 1 is buffered with a buffer having a conductivity of 10-50 mS·cm$^{-1}$.

29. The process of claim 1 wherein the first albumin solution treated in step (a) of claim 1 is buffered with a buffer having a conductivity of 18-22 mS·cm$^{-1}$.

30. The process of claim 1 wherein the first albumin solution treated in step (a) of claim 1 comprises albumin at a concentration of at least 70 g·L$^{-1}$.

31. The process of claim 14 wherein the albumin is loaded in step (a) of claim 1 in less than 0.5 column volumes.

32. The process of claim 1 wherein the albumin is loaded in step (a) of claim 1 in less than 0.35 column volumes.

33. The process of claim 1 wherein the matrix used in step (a) of claim 1 comprises immobilised boronic acid.

34. The process of claim 1 wherein the matrix used in step (a) of claim 1 comprises aminophenylboronic acid.

35. The process of claim 1 further comprising an anion exchange step, preferably utilising a matrix which comprises immobilised dialkylaminoalkyl substituents as anion exchangers, followed by a further diafiltration step that is conducted at a pH of 2.5-6.0.

36. The process of claim 35 wherein the anion exchange step is run in negative mode with respect to the albumin.

37. The process of claim 35 wherein the anion exchange step is run in positive mode with respect to the albumin.

38. The process of claim 36 wherein, prior to the anion exchange step, the albumin solution undergoes one or more of: buffer exchange; concentration; dilution; dialysis; diafiltration; pH-adjustment; treatment with a reducing agent; decolouration treatment; heating; cooling or a non-purifying handling step which improves the environment or condition of the albumin for the next step of the process or for final use.

39. The process of claim 37 wherein, prior to the anion exchange step, the albumin solution undergoes one or more of: buffer exchange; concentration; dilution; dialysis; diafiltration; pH-adjustment; treatment with a reducing agent; decolouration treatment; heating; cooling or a non-purifying handling step which improves the environment or condition of the albumin for the next step of the process or for final use.

40. The process of claim 1 which is preceded by one or more of the following steps: fermentation; separation of albumin from a recombinant albumin-producing host cell; subjecting a centrate from fermentation to a non-purifying handling step which improves the environment or condition of the albumin for the next step of the process or for final use; cation exchange chromatography; anion exchange chromatography; or affinity chromatography.

41. The process of claim 40, wherein the process of claim 1 is preceded by cation exchange chromatography using sulfopropyl substituents as cation exchangers.

42. The process of claim 40, wherein the process of claim 1 is preceded by anion exchange chromatography using diethylaminoalkyl substituents as anion exchangers.

43. The process of claim 40, wherein the process of claim 1 is preceded by affinity chromatography using an affinity matrix which comprises an immobilised albumin-specific dye.

44. The process of claim 43 in which the immobilised albumin-specific dye is a Cibacron Blue type of dye.

45. A process for purifying a recombinant albumin solution, the process comprising the steps of:
(a) subjecting a recombinant albumin solution to a cation exchange chromatography step run in positive mode with respect to the albumin;
(b) collecting an albumin-containing cation exchange eluate;
(c) subjecting the cation exchange eluate to an anion exchange chromatography step run in positive mode with respect to the albumin;
(d) collecting an albumin-containing anion exchange eluate;
(e) subjecting the anion exchange eluate to an affinity chromatography step run in positive mode with respect to the albumin;
(f) collecting an albumin-containing affinity chromatography eluate;
(g) subjecting the affinity chromatography eluate to an affinity chromatography step run in negative mode with respect to the albumin and in positive mode with respect to glycoconjugates according to step (a) of claim 1;
(h) collecting the albumin-containing affinity chromatography flow through;
(i) subjecting the affinity chromatography flow through to concentration, diafiltration and cation exchange chromatography steps according to step (b) of claim 1 to produce a recombinant albumin-containing cation exchange flow through having a nickel ion content of less than 100 ng per gram of albumin;
(j) collecting the albumin-containing cation exchange flow through;
(k) subjecting the cation exchange flow through to an anion exchange chromatography step run in negative mode or positive mode;
(l) collecting the albumin-containing anion exchange flow through wherein the anion exchange step is run in negative mode; or eluting from the anion exchange matrix an anion exchange eluate wherein the anion exchange step is run in positive mode; and
(m) a diafiltration step that is conducted at a pH of 2.5-6.0.

46. The process of claim 45 wherein any of steps (a) to (m) are preceded or followed by one or more of: buffer exchange; concentration; dilution; dialysis;
diafiltration; pH-adjustment; treatment with a reducing agent; decolouration treatment;
heating; cooling or a non-purifying handling step which improves the environment or condition of the albumin for the next step of the process or for final use.

47. A process for purifying a recombinant albumin solution, the process comprising the steps of:
(a) subjecting a recombinant albumin solution to a cation exchange chromatography step run in positive mode with respect to the albumin;
(b) collecting an albumin-containing cation exchange eluate;
(c) subjecting the cation exchange eluate to an anion exchange chromatography step run in positive mode with respect to the albumin;
(d) collecting an albumin-containing anion exchange eluate;
(e) subjecting the anion exchange eluate to an affinity chromatography step run in positive mode with respect to the albumin;
(f) collecting an albumin-containing affinity chromatography eluate;
(g) subjecting the affinity chromatography eluate to an affinity chromatography step run in negative mode with respect to the albumin and in positive mode with respect to glycoconjugates according to step (a) of claim 1;
(h) collecting the albumin-containing affinity chromatography flow through;
(i) subjecting the affinity matrix flow through to an anion exchange chromatography step run in negative or positive mode with respect to the albumin;
(j) collecting the albumin-containing anion exchange flow through wherein the anion exchange step is run in negative mode; or eluting from the anion exchange matrix an anion exchange eluate wherein the anion exchange step is run in positive mode;

(k) subjecting the albumin solution purified by the anion exchange chromatography step to concentration, diafiltration and cation exchange chromatography steps in accordance with step (b) of claim 1 to produce a recombinant albumin-containing cation exchange flow through having a nickel ion content of less than 100 ng per gram of albumin;

(l) collecting the albumin-containing cation exchange flow through.

48. The process of claim 47 wherein any of steps (a) to (l) are preceded or followed by one or more of: buffer exchange; concentration; dilution;

dialysis; diafiltration; pH-adjustment; addition of reducing agent; decolouration treatment; heating; cooling or a non-purifying handling step which improves the environment or condition of the albumin for the next step of the process or for final use.

49. The process of claim 1 wherein the recombinant albumin is produced by a process comprising culturing a fungal cell expressing a recombinant albumin coding sequence and obtaining the albumin, wherein the cell has a genetic modification in a coding region of a gene encoding a protein O-mannosyltransferase (PMT) enzyme or in a region involved in the expression of a gene encoding a PMT enzyme which causes the cell to have at least a reduced capacity of mannosylation of the recombinantly-expressed albumin and wherein the culture medium is at least 1,000 L and is of pH5.3-6.8.

50. The process of claim 49 wherein said modification(s) comprises any suppression, substitution, deletion, addition, disruption and/or mutational insertion.

51. The process of claim 50 wherein said modification(s) are stably-inherited and/or are non-reverting and/or are non-leaky.

52. The process of claim 49 wherein the gene encoding a PMT enzyme encodes PMT1.

53. The process of claim 49 wherein the fungal cell is cultured in a culture medium of at least 5,000 L.

54. The process of claim 53 wherein the fungal cell is cultured in a culture medium of at least 7,500 L.

55. The process of claim 49 wherein the fungal cell is cultured at pH 6.2-6.7.

56. The process of claim 55 wherein the fungal cell is cultured at pH 6.3-6.5.

57. The process of claim 1 wherein the initial albumin solution is derived from a yeast culture medium obtained by culturing yeast transformed with an albumin-encoding nucleotide sequence in a fermentation medium, whereby said yeast expresses albumin and secretes it into the medium.

58. The process of claim 57 wherein the yeast is of the genus *Saccharomyces*.

59. The process of claim 58 wherein the yeast is *Saccharomyces cerevisiae*.

60. The process of claim 57 wherein the yeast is of the genus *Pichia* or *Kluyveromyces*.

61. The process of claim 49 wherein the albumin is encoded by a DNA sequence which comprises a recombinant albumin coding sequence wherein the 3' end of the recombinant albumin coding sequence comprises two or more in-frame translation stop codons, and preferably three in-frame translation stop codons.

62. The process of claim 57 wherein the albumin is encoded by a DNA sequence which comprises a recombinant albumin coding sequence wherein the 3' end of the recombinant albumin coding sequence comprises two or more in-frame translation stop codons, and preferably three in-frame translation stop codons.

63. The process of any one of claim 1, 35, 45, 46, 47 or 48 wherein the albumin product is formulated for parenteral administration to a human, sterilised or placed into a final container.

* * * * *

```
                    SEQUENCE LISTING

<160> NUMBER OF SEQ ID NOS: 16

<210> SEQ ID NO 1
<211> LENGTH: 423
<212> TYPE: DNA
<213> ORGANISM: Artificial Sequence
<220> FEATURE:
<223> OTHER INFORMATION: Description of Artificial Sequence:DNA SEQUENCE
      HAVING HOMOLOGY TO THE PROTEIN ENCODING REGION
      SACCHAROMYCES CEREVISIAE PMT1

<400> SEQUENCE: 1
gattggcaga agaggtatct gcttatggac atgaggggct ttggcggtga tgccaatgat    60
gactttgttg tggagattgc caaggatctt tcaactactg aagaagctaa ggaaaacgtt   120
agggccattc aaactgtttt tagattgaga catgcgatga ctggttgtta cttgttctcc   180
cacgaagtca agcttcccaa gtgggcatat gagcaacaag aggttacttg tgctactcaa   240
ggtatcaaac cctatcttac tggtacgttg agaccaacga aacccattc ttggataaag    300 aggttgatga atagttagc tatcctgttc cgactttctt tcaaaggttg ccgactcacg    360
ccagaatgtg gaagatcaac aaggcttact gatcatatgc tatgaatcca gtccagatct   420
tgg                                                                  423

<210> SEQ ID NO 2
<211> LENGTH: 454
<212> TYPE: DNA
<213> ORGANISM: Artificial Sequence
<220> FEATURE:
<223> OTHER INFORMATION: Description of Artificial Sequence:DNA SEQUENCE
      HAVING HOMOLOGY TO THE PROTEIN ENCODING REGION
      SACCHAROMYCES CEREVISIAE PMT1

<400> SEQUENCE: 2
gtgttgcagt tgtagtccca cttgagtatc ttggattcgt tgcattggtc cttggtccat    60
cgtcctgcat agatcaatgg gagaatatct ttggaagata gaaagcgcaa cggcaaaaaa   120
gagaacgaat atggagtaag acacaacctg tttgtttttg aagacataag agtgaataat   180
ctcaaacaca tgtccgagag ccaatatacc aaagtacaat gatggtagat agtggtgcaa   240
aaatagctga cgggccataa gggaaagatg gcaagtaatg cagtacccat cctaggatgt   300
aatgaagcat tgaacattg aagttgagca cagttgggtc aacgctgaac ccaaaacctc    360
tttgcctctc agaatagaga aaccaaaaag acagagaaca aagcatactt gcggtgactg   420
tcaccaagtg acagcattcc tatgaaataa attg                                454

<210> SEQ ID NO 3
<211> LENGTH: 408
<212> TYPE: DNA
```

```
<213> ORGANISM: Artificial Sequence
<220> FEATURE:
<223> OTHER INFORMATION: Description of Artificial Sequence:DNA SEQUENCE
      WITH HOMOLOGY TO THE PROTEIN ENCODING REGION
      SACCHAROMYCES CEREVISIAE PMT7

<400> SEQUENCE: 3
tacgttatgg atgtgcatcc acttcctgaa gcttctcatc ggcaaccttt tgaatctgca      60
atttattatc ttcattgaag gcaagcttga acactttgac ggtagaaaga cgagcgacaa     120
ccaagaattg cccgtcagaa gtgagatcac aatgggtgat gttgtcctca tcgcttagga    180
ccagtttggc taatagtttt ctgccttgct gaggaaggac tttccatact ttaatggttt    240
ggtcttgccc atgatcacca gcttctggga tttattgaaa aggacagttt gatcgtttca    300
gggaatactg acagtctttg aatttcgcag tcttgaaacg attcagctta gaaacggcta    360
tgtctgacaa tgatgcttca gatagtacag atcgaggtcc tggattgg                 408

<210> SEQ ID NO 4
<211> LENGTH: 350
<212> TYPE: DNA
<213> ORGANISM: Artificial Sequence
<220> FEATURE:
<223> OTHER INFORMATION: Description of Artificial Sequence:DNA SEQUENCE
      HAVING HOMOLOGY TO THE PROTEIN ENCODING REGION
      SACCHAROMYCES CEREVISIAE PMT7

<400> SEQUENCE: 4
gcgcaggtga cttcttgctg gaaaatgtgc tacaaggagg taaagaccgt gtcattgagg      60
gcctggtttg gtctacttat gacgattacc ctcgtcgtct gttttccatt ggtggttcga    120
ctgtgatgac cgaatgggat attgctaccg gtttgccctt aaacaactac gattgtaact    180
ccggtatcac ctggagtatc agcatcaaca caactcagga taagatatgc gtaggctgtg    240
acaatggaac tgtagtcgtt attgacataa gtggtggacc gggatctcta gtataagaaa    300
attgtatccg gatgttctga tggccgataa ggatatggaa tacgaggaag                350

<210> SEQ ID NO 5
<211> LENGTH: 391
<212> TYPE: DNA
<213> ORGANISM: Artificial Sequence
<220> FEATURE:
<223> OTHER INFORMATION: Description of Artificial Sequence:DNA SEQUENCE
      HAVING HOMOLOGY TO THE PROTEIN ENCODING REGION
      SACCHAROMYCES CEREVISIAE PMT7

<400> SEQUENCE: 5
gtattgcagt tgtagtccca gaatgaattg ctcttttaat tgttcttttt ggctggagaa      60
gtgctcgtat gtcttgatcg atgagataca gctgagattt aagttgttct aggttgatag    120
ttgaatgttc agagttgagg ggttccatgg tcaagtatag gaggatccag ctcatctagg    180
gagtggaatt gagtactgac actcattact ggaagaagta gaaagagtac tggttttgtg    240
gtaagttcca tatttcagat gtctgtagat ggtcgagcga ggtgaacatt tcataggaga    300
tttcagagga gttggacttt gaaaatggtg acaaaaggta gacagaagaa aggttagaga    360
gtgcagtgat tcaaggtggt tgcagaagtc c                                    391

<210> SEQ ID NO 6
<211> LENGTH: 361
<212> TYPE: DNA
<213> ORGANISM: Artificial Sequence
<220> FEATURE:
<223> OTHER INFORMATION: Description of Artificial Sequence:DNA SEQUENCE
      HAVING HOMOLOGY TO THE PROTEIN ENCODING REGION
```

-continued

SACCHAROMYCES CEREVISIAE PMT7

<400> SEQUENCE: 6

```
ttgagacatg ctatgacggg tcaagttttt agataaagtt ggactcttgg gcatgagcgc    60
atcctcacat cggccatagc agataaacgg tagcagtttt tttgaacgag gctgtaagat   120
aggggaatct ccgttttagg ctttcagtga cttgttgcat cgcaatgggt agatatgttc   180
accagtggca aaagctctgg atgctatgaa actgaccaaa tgtggattag aacttggagt   240
ctaactattt gactctaaga atttccaatt tttgccttct actagccatt ttctactttc   300
atgggacatc atcacttatt tgctccccaa cctgtcaaat acccaccaat gttcaaggtc   360
g                                                                   361
```

<210> SEQ ID NO 7
<211> LENGTH: 386
<212> TYPE: DNA
<213> ORGANISM: Artificial Sequence
<220> FEATURE:
<223> OTHER INFORMATION: Description of Artificial Sequence:DNA SEQUENCE
WITH HOMOLOGY TO THE PROTEIN ENCODING REGION
SACCHAROMYCES CEREVISIAE PMT5

<400> SEQUENCE: 7

```
agattgagac atgctatgac gggttgttac ttgttctccc gcgaagtcaa gcttcccaag    60
tgggcatatg agcaacaaga ggttacttgt gctactcaag ggtatcaaac cactatctta   120
ctggtacgtt gagaccaacg aaaacccatt cttggataaa gaggttgatg aaatagttag   180
ctatcctgtt ccgactttct ttcaaaaggt tgccgagcta cacgccagaa tgtggaagat   240
caacaagggc ttaactgatc atcatgtcta tgaatccagt ccagattctt ggcccttcct   300
gtcagaggta taagctactg gtcaaaaaat cactccaaat tatttcatag gtaatgctgc   360
acttggtgga cagtcaccga agtttg                                         386
```

<210> SEQ ID NO 8
<211> LENGTH: 406
<212> TYPE: DNA
<213> ORGANISM: Artificial Sequence
<220> FEATURE:
<223> OTHER INFORMATION: Description of Artificial Sequence:DNA SEQUENCE
HAVING HOMOLOGY TO THE PROTEIN ENCODING REGION
SACCHAROMYCES CEREVISIAE PMT5
<220> FEATURE:
<221> NAME/KEY: misc_feature
<222> LOCATION: (122)..(122)
<223> OTHER INFORMATION: n is a, c, g, or t

<400> SEQUENCE: 8

```
gtgttgcagt tgtagtccca cttgagtatc ttggattcgt tgcattggtc cttggtccat    60
cgtcctgcat agatcaatgg gagaatatct ttggaagaag aaagcgcaac ggcaaaaaag   120
anaacgaata tggagtaaga cacaacctgt tgtttttga agacataaga gtgaataatc   180
tcaaacacat gtccgagagc caatatacca agtacaatg atggtagata gtgggtgcaa   240
aaatagctga cgggccataa ggaaagatgg caagtaatgc agtacccatc ctaggatgta   300
atgaagcatt tgaacattga agttgaacac agttgggtca acgctgaacc caaaacctct   360
ttgccatctc agaatagaga aaaccaaaaa gacagagaac aaagca                   406
```

<210> SEQ ID NO 9
<211> LENGTH: 21
<212> TYPE: DNA
<213> ORGANISM: Artificial Sequence
<220> FEATURE:

<223> OTHER INFORMATION: Description of Artificial Sequence: MODIFIED
      ALBUMIN CODING SEQUENCE

<400> SEQUENCE: 9
ttagcctgat aataagctta a                                              21

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence:PCR PRIMER

<400> SEQUENCE: 10
gcataagctt tggacttctt cgccagaggt ttggtcaag                           39

<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence:PCR PRIMER

<400> SEQUENCE: 11
tggacaacat tagcaagaag gtgtgcctag cgccggcgcc taggtacg                 48

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:PCR PRIMER

<400> SEQUENCE: 12
agtccaagct taattcttat gatttatgat                                     30

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence:PCR PRIMER

<400> SEQUENCE: 13
cagcactgac ccttttg                                                   17

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence:
      OLIGONUCLEOTIDE LINKER

<400> SEQUENCE: 14
ttaagagtcc aagccttagg cttataata                                      29

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence:
      OLIGONUCLEOTIDE LINKER

<400> SEQUENCE: 15
ctcaggttcg gaatccgaat attattcga                                      29

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence:PORTION OF
      PEPTIDE ENCODED BY LINER SEQUENCE

<400> SEQUENCE: 16

Ala Leu Gly Leu
1